(12) United States Patent
Slishman

(10) Patent No.: US 11,246,602 B2
(45) Date of Patent: Feb. 15, 2022

(54) PRESSURE WRAPS AND METHODS OF USING PRESSURE WRAPS

(71) Applicant: Samuel Slishman, San Luis Obispo, CA (US)

(72) Inventor: Samuel Slishman, San Luis Obispo, CA (US)

(*) Notice: Subject to any disclaimer, the term of this patent is extended or adjusted under 35 U.S.C. 154(b) by 218 days.

(21) Appl. No.: 16/827,295

(22) Filed: Mar. 23, 2020

(65) Prior Publication Data

US 2020/0305891 A1     Oct. 1, 2020

Related U.S. Application Data

(60) Provisional application No. 62/824,828, filed on Mar. 27, 2019.

(51) Int. Cl.
*A61B 17/132* (2006.01)
*A61B 17/12* (2006.01)
(Continued)

(52) U.S. Cl.
CPC .......... *A61B 17/1327* (2013.01); *A61B 90/94* (2016.02); *A61B 2017/00424* (2013.01); *A61B 2017/12004* (2013.01)

(58) Field of Classification Search
CPC .............. A61B 17/132; A61B 17/1322; A61B 17/1327; A61B 2017/12004
See application file for complete search history.

(56) References Cited

U.S. PATENT DOCUMENTS 1,473,041 A    11/1923    Henderson
2,519,712 A     8/1950    Stegeman
(Continued)

FOREIGN PATENT DOCUMENTS

CN    201624718 U    11/2011
CN    202960644 U     6/2013
(Continued)

OTHER PUBLICATIONS

Machine-generated English language translation of Japan Patent No. JP 08011588 B2, Global Patent Solutions, Mar. 3, 2017.
(Continued)

*Primary Examiner* — Ryan J. Severson
(74) *Attorney, Agent, or Firm* — Dascenzo Gates Intellectual Property Law, P.C.

(57) ABSTRACT

Pressure wraps include an elongated elastic strap and an adjustable loop formed in the elongated elastic strap. The elongated elastic strap is wrapped around a subject to form a plurality of loops, and provides selectively variable amounts of pressure depending on the amount of tension applied to the elongated elastic strap as the loops are formed around the subject. The size of the adjustable loop is configured to be selectively varied via an adjustment component. Pressure wraps may include a plurality of discrete regions of hooks compatible with the pile of the elongated elastic strap, which are configured to inhibit unintentional unwrapping during application. A securement is configured to secure the distal end of the elongated elastic strap to an intermediate portion of the strap, thereby securing the pressure wrap with respect to the subject. The securement may include a manipulatable fastener and/or an automatic fastener for securing the strap.

26 Claims, 10 Drawing Sheets

(51) Int. Cl.
*A61B 17/00* (2006.01)
*A61B 90/94* (2016.01)

(56) References Cited

U.S. PATENT DOCUMENTS

| | | | |
|---|---|---|---|
| 3,059,645 A | | 10/1962 | Hasbrouck et al. |
| 3,086,529 A | * | 4/1963 | Munz .................... A61F 13/10 |
| | | | 606/203 |
| 3,390,680 A | * | 7/1968 | Marcum ............ A61B 17/1322 |
| | | | 606/203 |
| 3,586,001 A | | 6/1971 | Sanderson |
| 3,628,536 A | | 12/1971 | Glesne |
| 4,149,540 A | * | 4/1979 | Hasslinger ......... A61B 17/1322 |
| | | | 128/DIG. 15 |
| 4,182,338 A | | 1/1980 | Stanulis |
| 4,635,635 A | | 1/1987 | Robinette-Lehman |
| 4,880,016 A | | 11/1989 | Worth et al. |
| 4,997,438 A | | 3/1991 | Nipper |
| 5,120,300 A | * | 6/1992 | Shaw ................ A61B 17/1322 |
| | | | 128/876 |
| 5,234,459 A | | 8/1993 | Lee |
| 5,295,996 A | | 3/1994 | Blair |
| 5,695,520 A | | 12/1997 | Bruckner et al. |
| 6,746,470 B2 | | 6/2004 | McEwen et al. |
| 6,752,820 B1 | | 6/2004 | Hafemann |
| 7,582,102 B2 | | 9/2009 | Heinz et al. |
| 7,652,190 B2 | | 1/2010 | Johnson |
| 7,663,015 B2 | | 2/2010 | Johnson |
| 7,776,064 B2 | | 8/2010 | Jennifer et al. |
| 7,842,067 B2 | | 11/2010 | Esposito |
| 7,892,253 B2 | | 2/2011 | Esposito et al. |
| D649,642 S | | 11/2011 | Johnson |
| 8,163,973 B2 | | 4/2012 | Johnson |
| 8,303,620 B2 | | 11/2012 | Johnson et al. |
| 8,641,690 B2 | | 2/2014 | Fitzpatrick et al. |
| 8,834,517 B2 | | 9/2014 | Croushorn et al. |
| D733,306 S | | 6/2015 | Blankenship |
| 9,259,212 B2 | | 2/2016 | Teeslink et al. |
| 10,194,917 B1 | * | 2/2019 | Carson .............. A61B 17/1327 |
| 10,335,160 B1 | * | 7/2019 | Holloman .......... A61B 17/1322 |
| 10,793,329 B2 | * | 10/2020 | Grady ................ A44B 18/0084 |
| 11,090,060 B2 | * | 8/2021 | Carson .............. A61B 17/1327 |
| 11,185,338 B2 | * | 11/2021 | Johnston .......... A61B 17/12109 |
| 2004/0092999 A1 | * | 5/2004 | Lojewski ........... A61B 17/1325 |
| | | | 606/185 |
| 2006/0201522 A1 | * | 9/2006 | Sato ................... A61B 17/1322 |
| | | | 128/898 |
| 2006/0211976 A1 | * | 9/2006 | Ramsey ............... A61F 15/006 |
| | | | 602/75 |
| 2007/0088385 A1 | * | 4/2007 | Perry ................. A61B 17/1322 |
| | | | 606/203 |
| 2008/0243173 A1 | * | 10/2008 | Thorpe .............. A61B 17/1322 |
| | | | 606/203 |
| 2012/0150215 A1 | | 6/2012 | Donald |
| 2014/0228732 A1 | | 8/2014 | Steinbaugh et al. |
| 2015/0080943 A1 | | 3/2015 | Ye |
| 2016/0296239 A1 | | 10/2016 | Bakhtyari-Nejad-Esfahani et al. |
| 2019/0274693 A1 | * | 9/2019 | Carson .............. A61B 17/1327 |
| 2020/0305891 A1 | * | 10/2020 | Slishman ........... A61B 17/1322 |
| 2021/0059687 A1 | * | 3/2021 | Johnston ........... A61B 17/1325 |
| 2021/0137532 A1 | * | 5/2021 | Kirkham ............ A61B 17/1322 |
| 2021/0315589 A1 | * | 10/2021 | Carson .............. A61B 17/1327 |

FOREIGN PATENT DOCUMENTS

| | | |
|---|---|---|
| GB | 211048 | 2/1924 |
| JP | 08011588 B2 | 2/1996 |
| WO | WO 2012/155372 A1 | 11/2012 |

OTHER PUBLICATIONS

Machine-generated English language translation of China Utility Model No. CN 201624718 U, Global Patent Solutions, Mar. 3, 2017.

Machine-generated English language translation of PCT Patent Publication No. WO 2012/155372 A1, Global Patent Solutions, Mar. 3, 2017.

Machine-generated English language translation of China Utility Model No. CN 202960644 U, Global Patent Solutions, Mar. 3, 2017.

Airwrap, RevMedX, accessed on Feb. 21, 2017 from http://www.revmedx.com/airwrap. Admitted Prior Art.

Another Chance Tourniquet, accessed on Feb. 28, 2018 from http://www.acttourniquet.com/index.html. Admitted Prior Art.

CAT Resources, Combat Application Tourniquet®, accessed on Feb. 14, 2017 from http://www.combattourniquet.com. Admitted Prior Art.

CE marked ELEO Latex Free Tourniquet, Quick Release Buckle Tourniquet, Disposable Tourniquet, accessed on Mar. 3, 2017 from https://alibaba.com/product-detail/CE-marked-ELEO-Latex-Free-Tourniquet_60329218627.html. Admitted Prior Art.

Disposable Medical Silicone Tourniquet Straps, Xiamen Better Silicon Import and Export Co., Ltd., accessed on Mar. 3, 2017 from http://bettersilicone.en.made-in-china.com/product/IMZmJTtdZwpj/China-Disposable-Medical-Silicone-Tourniquet-Straps.html. Admitted Prior Art.

Disposable Tourniquet, Shenzhen TMI Technology Co., Ltd., TAMI Medical, accessed on Mar. 3, 2017 from http://www.sztmi.com/en/productsview.asp?id=51&cid=001. Admitted Prior Art.

Guardian Tourniquet Belt, accessed on Mar. 3, 2020 from https://myguardianbelt.com. Admitted Prior Art.

The Israeli Bandage®, PerSys Medical, accessed on Mar. 3, 2020 from https://persysmedical.com/products/hemorrhage-control/. Admitted Prior Art.

M2® Ratcheting Medical Tourniquets®, accessed on Feb. 14, 2017 from https://www.ratchetingbuckles.com/applications/military/medical-tourniquets/. Admitted Prior Art.

MAT Combat Tourniquet, Pyng Medical, accessed on Feb. 14, 2017 from http://www.pyng.com/products/matcombat/. Admitted Prior Art.

MDM—Cinch Tourniquets, Soldier Systems Daily, accessed on Feb. 14, 2017 from http://soldiersystems.net/2011/09/27/mdm-cinch-tourniquets/. Admitted Prior Art.

OLAES® Modular Bandage, Tactical Medical Solutions, accessed on Mar. 3, 2020 from https://www.tacmedsolutions.com/OLAES-Modular-Bandage. Admitted Prior Art.

PAX Extremities Tourniquet, accessed on Mar. 3, 2020 from https://www.pax-bags.com/shop/en/pax-extremitaten-tourniquet/. Admitted Prior Art.

Prometheus FullStop Tourniquet, accessed Mar. 23, 2020 from https://www.prometheusmedical.co.uk/equipment/prometheus-equipment-haemorrhage-control/prometheus-fullstop-tourniquet-0. Admitted Prior Art.

RapidStop Tourniquet, accessed Mar. 23, 2020 from https://us.rapid-stop.com/. Admitted Prior Art.

R.A.T.S. Tourniquet, RATS Medical, accessed on Mar. 3, 2020 from https://ratsmedical.com. Admitted Prior Art.

Riester 11223 Cuff, Thigh, Pneumatic Tourniquet, Medequip Depot, accessed on Mar. 3, 2020 from https://www.medequipdepot.com/products/11223-riester-cuff-thigh-pneumatic-tourniquet.html. Admitted Prior Art.

SAM XT Tourniquet, SAM Medical, accessed on Mar. 3, 2020 from https://www.sammedical.com/products/sam-xt. Admitted Prior Art.

SICH Tourniquet, Sich Tourniquet USA, accessed on Mar. 5, 2020 from https://sichtourniquet.com. Admitted Prior Art.

SOF® Tactical Tourniquet, Tactical Medical Solutions, accessed on Feb. 28, 2020 from https://www.tacmedsolutions.com/SOF-Tactical-Tourniquet. Admitted Prior Art.

SOF® Tourniquet GEN 4, Tactical Medical Solutions, accessed on Mar. 3, 2020 from https://www.tacmedsolutions.com/SOF-Tourniquet-Gen-4. Admitted Prior Art.

SWAT-T™ Stretch Wrap and Tuck Tourniquet, accessed on Mar. 4, 2020 from https://www.swat-t.com/products.html. Admitted Prior Art.

TacMed™ K9 Tourniquet, Tactical Medical Solutions, accessed on Mar. 3, 2020 from https://www.tacmedsolutions.com/TacMed-K9-Tourniquet. Admitted Prior Art.

(56) References Cited

OTHER PUBLICATIONS

Tactical Compression Wrap, North American Rescue, accessed on Mar. 3, 2020 from http://www.narescue.com/tactical-compression-wrap.html. Admitted Prior Art.
THOR TQ Tourniquet, accessed on Feb. 14, 2017 from https://www.thortq.com/. Admitted Prior Art.
TK-4 Easy, Lightweight Tourniquet, H&H Medical Corporation, accessed on Mar. 3, 2020 from https://buyhandh.com/products/tk-4-compression-strap. Admitted Prior Art.
TMT™ Tourniquet, Combat Medical Systems, accessed on Mar. 3, 2020 from https://combatmedical.com/product/tmt-tourniquet/. Admitted Prior Art.
TX2™ TX3™, RevMedX, accessed on Feb. 14, 2017 from http://www.revmedx.com/rmx-tourniquet. Admitted Prior Art.
"Why Israeli Bandages are like Pepperidge Farm Bread," Imminent Threat Solutions, accessed on Feb. 14, 2017 from http://www.itstactical.com/medcom/medical/why-israeli-bandages-are-like-pepperidge-farm-bread/. Admitted Prior Art.
X8T Tourniquet, RCR Medical, accessed on Mar. 3, 2020 from https://www.rcrmedic.com/x8t-tourniquet. Admitted Prior Art.

\* cited by examiner

PRESSURE WRAPS AND METHODS OF USING PRESSURE WRAPS

RELATED APPLICATION

This application claims priority to U.S. Provisional Patent Application Ser. No. 62/824,828, which was filed on Mar. 27, 2019, the complete disclosure of which is hereby incorporated by reference for all purposes.

FIELD

The present disclosure is directed generally to pressure wraps and to methods of using pressure wraps.

BACKGROUND

Hemostasis, or bleeding control, is often critical in trauma situations. To achieve hemostasis, pressure wraps may be used to apply direct pressure to wounds, while tourniquets are applied proximal to wounds to temporarily stop arterial blood flow until patients are transported to hospitals or other medical facilities for treatment.

A number of different types of tourniquets are available, though many are associated with one or more significant disadvantages. For example, windlass tourniquets are applied by wrapping a belt or strap around the patient and then twisting a mechanism to ratchet up the pressure applied by the tourniquet. Such windlass tourniquets require training for proper use, and often require a great deal of force to be applied when forming the first loop in order to be effective. Such force requirements may be painful to the patient and/or may be difficult to apply. Furthermore, applying a windlass tourniquet in an incorrect orientation can increase discomfort for the patient and/or reduce the effectiveness of the tourniquet. The pressure applied by windlass tourniquets often may only be increased incrementally, or in a stepwise manner, such as by 180 degree turns of the ratcheting mechanism.

Many types of tourniquets run the risk of crushing the patient's tissue, causing pain, limb ischemia, and/or pinching or pulling of the patient's skin while the tourniquet is applied. Even further, medical personnel often find that tourniquets could have been removed long before the patient arrives at the hospital or medical facility. Conventional tourniquets, however, do not provide for gentle removal of the tourniquet, or for gradual reduction in the pressure applied by the tourniquet. Thus, tourniquets may cause unnecessary pain and/or tissue damage by being left on a wound long after bleeding clots or stops.

As a further disadvantage, many conventional tourniquets come in multiple different sizes, causing medical responders to carry multiple different sizes with them and/or have to try to choose the appropriate size in emergency situations where time is critical. Complicated mechanisms for tightening the tourniquets also increase costs and/or may be difficult for one in the field to apply one-handed (e.g., to himself or herself).

SUMMARY

Presently disclosed pressure wraps are configured to apply a pressure to a subject and certain examples may address one or more disadvantages of prior art tourniquets and pressure wraps. The pressure wraps of the present disclosure generally are configured for use in applying direct pressure to a wound, though they may be configured for use as a tourniquet as well. Said pressure wraps include an elongated elastic strap and an adjustable loop formed in the elongated elastic strap. The elongated elastic strap has a length extending longitudinally from a proximal end to a distal end, with the elongated elastic strap having a first side and a second side opposite the first side. At least a portion of the first side and/or the second side of the elongated elastic strap includes pile compatible with hook-and-loop fasteners. Further, the length of the elongated elastic strap is sufficient to allow the elongated elastic strap to be wrapped around the subject to form a plurality of loops. To apply the pressure wrap to the subject, the elongated elastic strap is configured to be selectively and reversibly extended (i.e., stretched) as it is wrapped around the subject to form the plurality of loops.

The adjustable loop is configured to be selectively increased or decreased via an adjustment component, and the adjustable loop is configured to be applied to the subject as the first loop of the plurality of loops. Disclosed pressure wraps also may include a plurality of discrete regions of hooks compatible with the pile of the elongated elastic strap, where the plurality of discrete regions of hooks are spaced apart from each other along the length of the elongated elastic strap. Disclosed pressure wraps also include a securement configured to selectively and removably secure the distal end of the elongated elastic strap to an intermediate portion of the elongated elastic strap, thereby securing the pressure wrap with respect to the subject. The securement is configured to maintain the pressure wrap in position after it is applied to the subject, and the securement may include a manipulatable fastener that is hand-operated to secure the distal end of the elongated elastic strap. In some examples, the securement includes an automatic fastener that automatically secures the distal end of the elongated elastic strap to the intermediate portion when the distal end is brought to contact the intermediate portion.

In some examples, the adjustment component is a buckle to which the elongated elastic strap may be engaged in such a way as to form the adjustable loop and then allow for the elongated elastic strap to be wrapped around the subject to form the plurality of loops. In some examples, the adjustment component is a sleeve through which the elongated elastic strap may slide (e.g., translate with respect to) in order to adjust the size of the adjustable loop. The present disclosure also includes methods of using or applying such pressure wraps, which may be configured for one-handed application in some instances. Methods also may include applying the disclosed pressure wraps in a position relative to a wound to apply direct pressure to the wound, or applying the disclosed pressure wraps proximal to a wound to serve as a tourniquet. The methods may include adjusting the width of a compression zone over which the pressure wrap applies pressure to the subject, such as to selectively increase or decrease the pressure applied by the pressure wrap, and/or to selectively spread out the pressure applied by the pressure wrap over a larger area of the subject.

DETAILED DESCRIPTION

Figure 1:
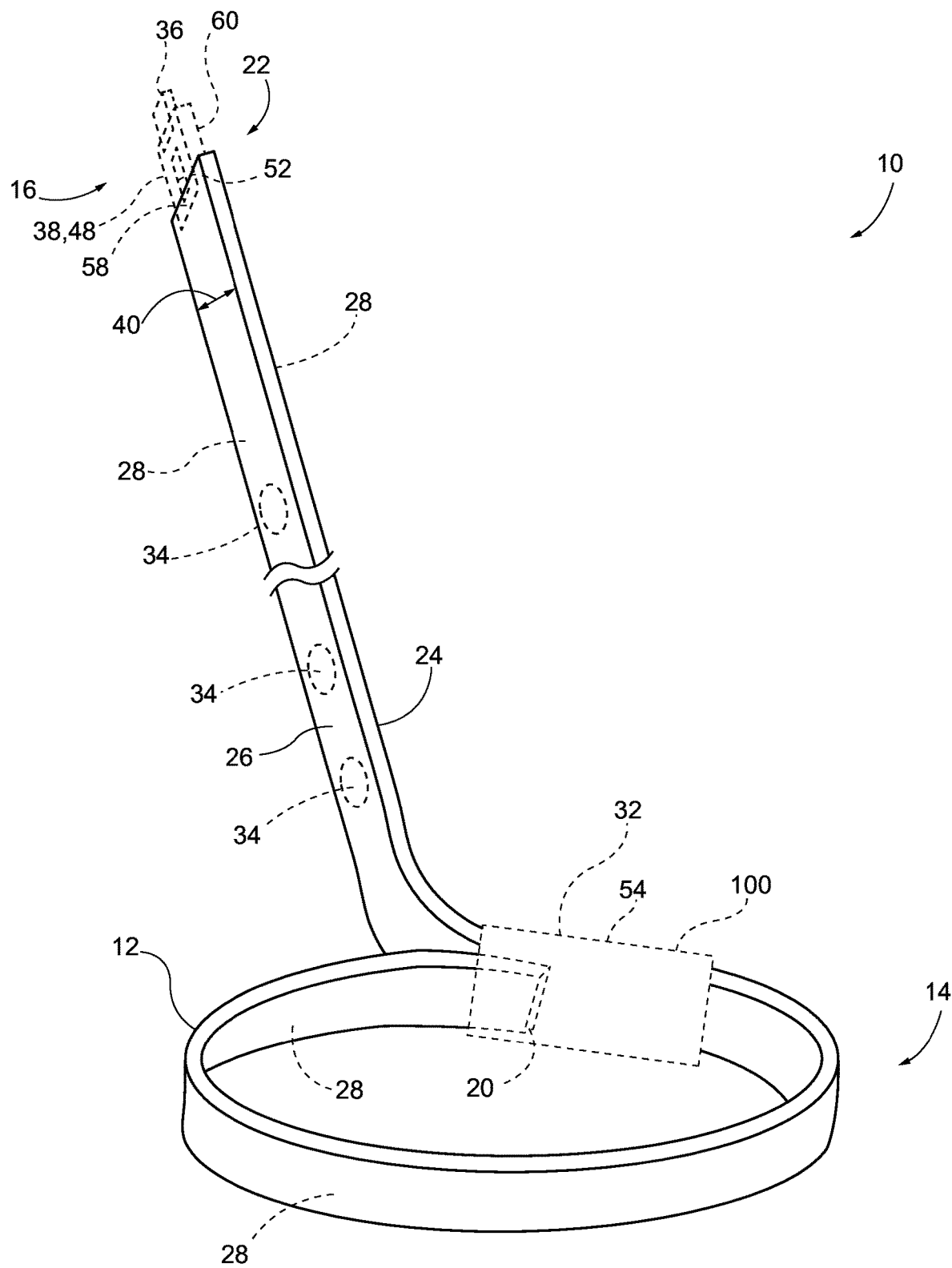
FIG. 1 is a schematic representation of examples of pressure wraps according to the present disclosure.

FIGS. 1-16 provide examples of pressure wraps 10 according to the present disclosure, and/or components of such pressure wraps 10. Elements that serve a similar, or at least substantially similar, purpose are labeled with like numbers in each of FIGS. 1-16, and these elements may not be discussed in detail herein with reference to each of FIGS. 1-16. Similarly, all elements may not be labeled in each of FIGS. 1-16, but reference numerals associated therewith may be utilized herein for consistency. One or more elements, components, and/or features that are discussed herein with reference to one or more of FIGS. 1-16 may be included in and/or utilized with any of FIGS. 1-16 without departing from the scope of the present disclosure. In general, elements that are likely to be included in a given (i.e., a particular) example are illustrated in solid lines, while elements that are optional to a given example are illustrated in dashed lines. However, elements that are shown in solid lines are not essential to all embodiments, and an element shown in solid lines may be omitted from a particular embodiment without departing from the scope of the present disclosure.

FIG. 1 provides a schematic representation of examples of pressure wraps 10, which include an elongated elastic strap 12, an adjustable loop 14 formed in elongated elastic strap 12, and a securement 16. In use, adjustable loop 14 is positioned with respect to a subject (e.g., placed on a limb of the subject), and then elongated elastic strap 12 is wrapped around the subject to form a plurality of loops.

Elongated elastic strap 12 is elastic, such that it is configured to be selectively and reversibly extended (e.g., stretched) as it is wrapped around the subject. The amount of pressure applied by pressure wrap 10 may be selectively increased or decreased by varying the amount of tension applied to elongated elastic strap 12 as it is wrapped around the subject to form the plurality of loops. Disclosed pressure wraps 10 may thus effectively provide for improved fine adjustability of the pressure applied to a subject, as compared to conventional windlass tourniquets, which generally only allow for coarse adjustment of the pressure through a limited number of discrete adjustment points (e.g., by turning a ratchet mechanism 180 degrees at a time).

Elongated elastic strap 12 has a length 18 (FIG. 7) extending longitudinally from a proximal end 20 of elongated elastic strap 12 to a distal end 22 of elongated elastic strap 12. Generally, proximal end 20 forms part of adjustable loop 14, while distal end 22 is at the opposite end of elongated elastic strap 12 and is secured to elongated elastic strap 12 via securement 16 once pressure wrap 10 is applied to a subject. As used herein, pressure wrap 10 may be said to be "applied to a subject" when elongated elastic strap 12 is made to form a plurality of loops around a subject, an appendage of a subject, a trunk of a subject, a limb of a subject, and/or a head of a subject, in order to apply pressure to the subject. The subject to which the pressure wrap is applied is a living organism, such as a human or an animal. As discussed herein, the adjustable nature of pressure wraps 10 enables them to be used with subjects having much different sizes and/or much differently sized limbs or other body parts to which the pressure wraps are applied.

Elongated elastic strap 12 includes a first side 24 and a second side 26 opposite first side 24. At least a portion of first side 24 of elongated elastic strap 12 may include pile 28 (sometimes referred to as "loops") compatible with hook-and-loop fasteners (which also may be referred to as hook-and-pile fasteners, touch fasteners, or simply Velcro™ fasteners).

Additionally or alternatively, at least a portion of second side 26 of elongated elastic strap 12 may include pile 28 compatible with hook-and-loop fasteners. In other words, in some examples of pressure wrap 10, just one of first side 24 and second side 26 includes pile 28, while in other examples, both first side 24 and second side 26 include pile 28. While examples herein are generally described as including pile 28 on one or both sides of elongated elastic strap 12, alternate embodiments wherein one or both sides of elongated elastic strap 12 include hooks for hook-and-loop fasteners also are within the scope of the present disclosure.

Figure 5:
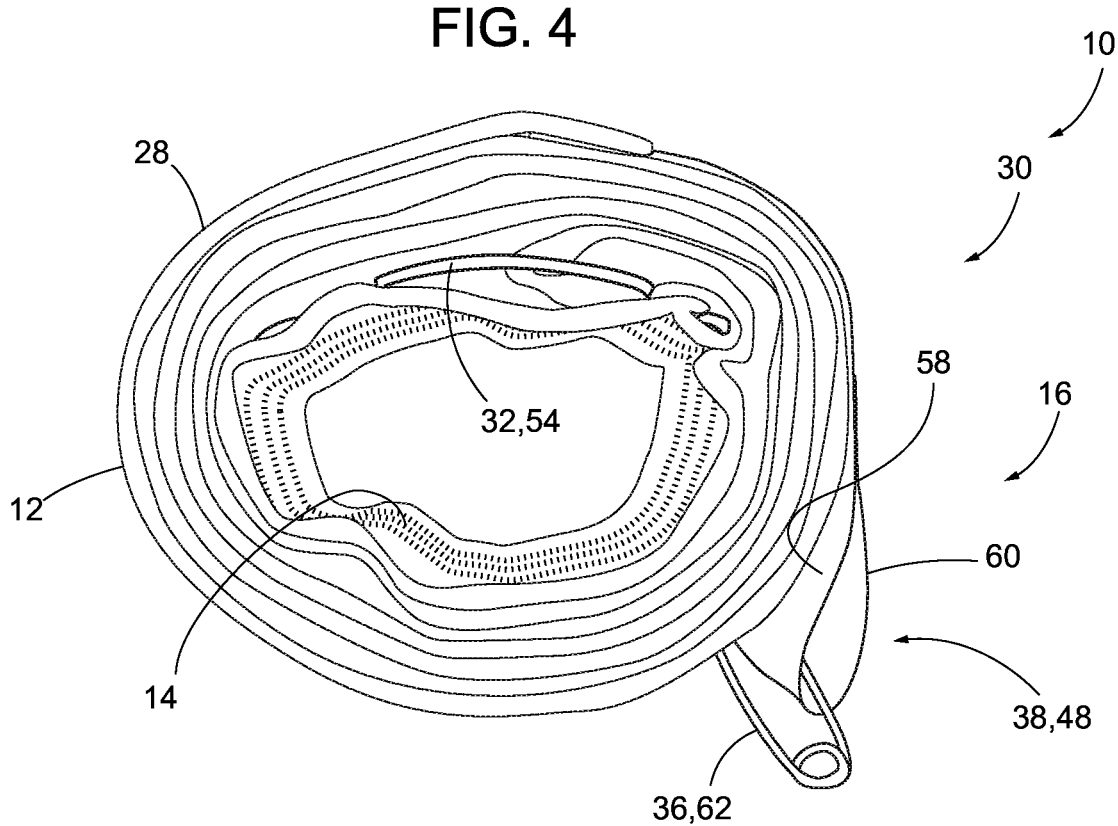
FIG. 5 is a side elevation view of a pressure wrap in an applied configuration, having been wrapped in a plurality of loops.
Figure 7:
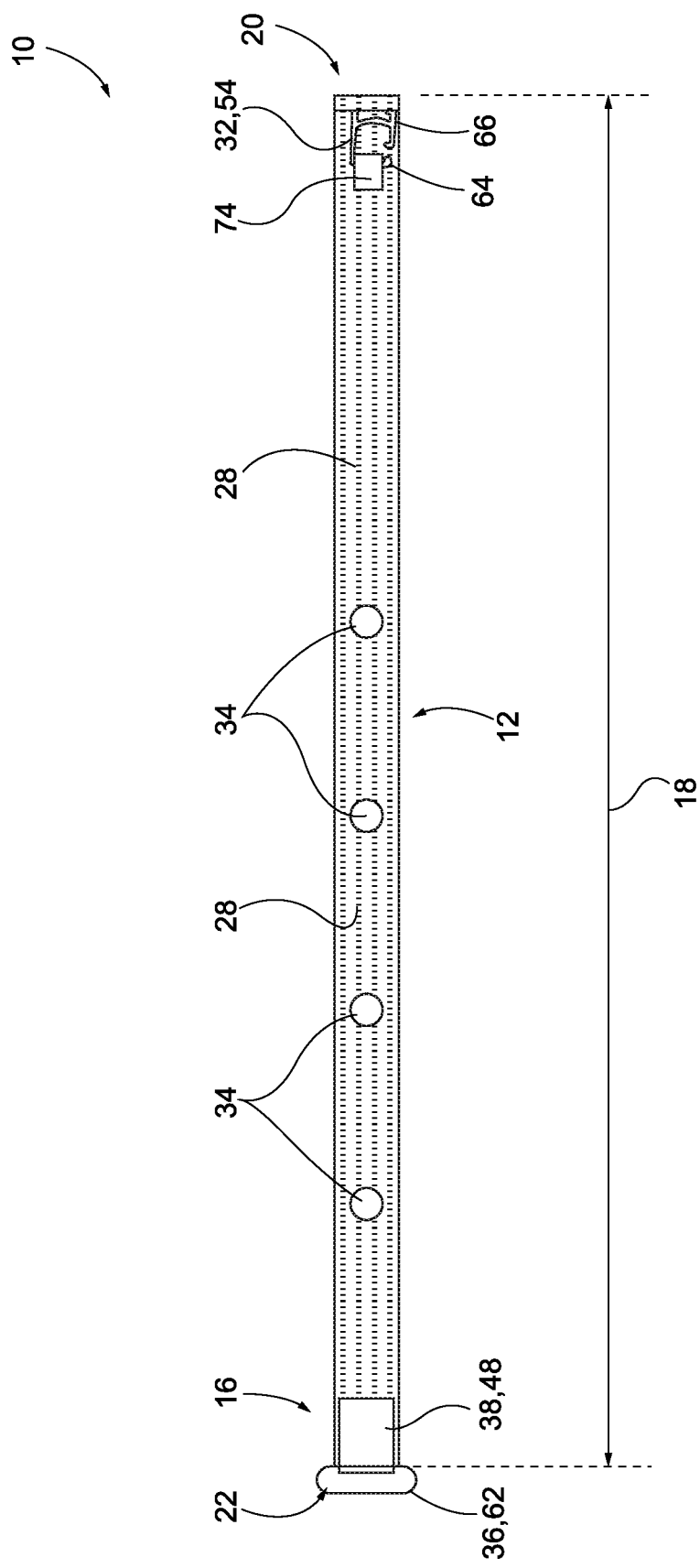
FIG. 7 shows a top plan view of an example of a pressure wrap, shown extended out in a resting configuration.

Elongated elastic strap 12 is configured such that its length 18 (such as shown in FIG. 7) is generally sufficient to allow elongated elastic strap 12 to be wrapped around the subject to form a plurality of loops 30 (an example of said plurality of loops 30 is shown in FIG. 5). For example, length 18 may be sufficient to form at least two, at least three, at least four, at least five, at least six, at least seven, at least eight, at least nine, and/or at least ten loops around a subject, such as around a subject's arm or leg. Each loop formed with elongated elastic strap 12 may effectively be independent from each other loop of plurality of loops 30, in the sense that the tension applied to elongated elastic strap 12 may be selectively varied with each individual loop formed.

Figure 4:
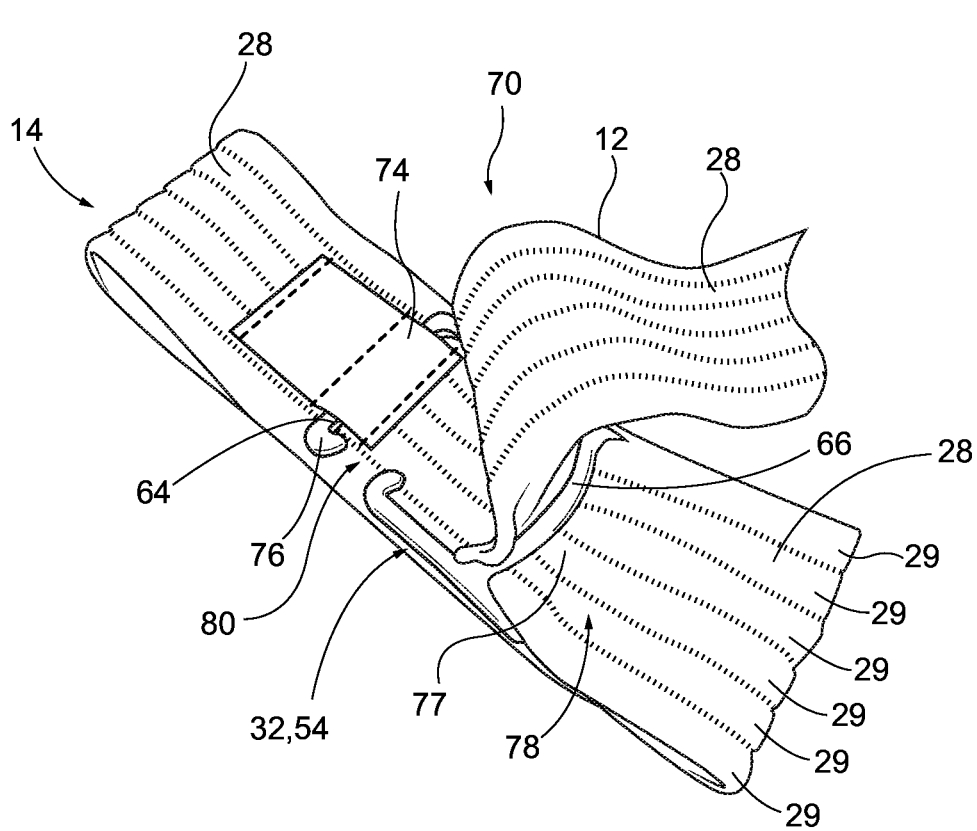
FIG. 4 is a perspective view of an example of a pressure wrap, with the strap engaged with an adjustment component in the form of a buckle.

In some examples, elongated elastic strap 12 has pile 28 along at least substantially the entire length 18 of elongated elastic strap 12, on one or both sides 24, 26 of the strap. Additionally or alternatively, elongated elastic strap 12 may have pile 28 covering at least a majority of a strap width 40, on first side 24 and/or second side 26 of elongated elastic strap 12, with strap width 40 being perpendicular to length 18 of elongated elastic strap 12. In some cases, pile 28 may be arranged in one or more strips 29 of pile 28, with said strips 29 being at least substantially parallel to length 18 in some examples (for example, FIG. 4 illustrates six strips 29 arranged parallel to length 18 of elongated elastic strap 12). Other orientations of said strips 29 of pile 28 also are within the scope of the present disclosure, such as strips 29 of pile 28 being at least substantially parallel to strap width 40 of elongated elastic strap 12, and/or strips 29 of pile 28 being arranged into shapes or oriented in non-parallel and non-perpendicular angles with respect to length 18 of elongated elastic strap 12.

The size of adjustable loop 14 is configured to be selectively increased or decreased via an adjustment component 32. Adjustable loop 14 may be pre-formed in pressure wrap 10 such that it is already formed when a user removes the pressure wrap from its packaging and/or when the user begins to apply pressure wrap 10 to a subject (or to the user him/herself). In some examples, the user may form adjustable loop 14 in pressure wrap 10 before applying pressure wrap 10 to a subject (or to the user him/herself). In some examples, pressure wrap 10 may be applied to a subject simply by wrapping elongated elastic strap 12 with respect to the subject without forming adjustable loop 14 (and/or without adjustment component 32). Though generally, adjustable loop 14 is configured to be applied to the subject as the first loop of the plurality of loops. For example, when applying pressure wrap 10 to a subject's arm, adjustable loop 14 may be positioned on the subject's arm and the size of adjustable loop 14 may be increased or decreased to create the desired fit with respect to the subject's arm. Adjustable loop 14 may be cinched, or tightened, until it is sized relative to the subject's limb to apply a pressure to the subject's limb, though generally the presently disclosed pressure wraps 10 need not be tightened to the extent that many conventional tourniquets require. Then, the remainder of elongated elastic strap 12 may be wrapped around the subject's arm until the entire pressure wrap 10 is wrapped in a plurality of loops around the subject's arm. In some examples, however, pressure wrap 10 may be applied to a subject without wrapping the entire length of elongated elastic strap 12 about the subject. When wrapping elongated elastic strap 12 to form the plurality of loops, each respective loop of the plurality of loops may be substantially concentric with (e.g., positioned on top of) the previous loops, or one or more loops of the plurality of loops may be disbursed or spread out, to distribute the pressure applied by pressure wrap 10, as will be described in more detail below.

Pressure wrap 10 also includes a plurality of discrete regions of hooks 34, with said hooks 34 being compatible with pile 28 of elongated elastic strap 12. The plurality of discrete regions of hooks 34 generally are spots of material comprising hooks that are spaced apart from each other along the length of elongated elastic strap 12, and the plurality of discrete regions of hooks 34 may be configured to prevent or inhibit unintentional reduction in pressure (e.g., unintentional unwrapping or unrolling of the plurality of loops) applied by pressure wrap 10. For example, each respective discrete region of hooks 34 may couple to pile 28 in a given segment of elongated elastic strap 12 as the portion of elongated elastic strap 12 that includes the respective discrete region of hooks 34 is wrapped around the subject. Thus, if application of pressure wrap 10 is interrupted (e.g., due to a user dropping or losing grip on elongated elastic strap 12), then discrete regions of hooks 34 that have been brought to contact prior loops of elongated elastic strap 12 may prevent pressure wrap 10 from losing tension and/or falling off of the subject. Additionally or alternatively, discrete region of hooks 34 may limit complete unrolling of pressure wrap 10 during application of the pressure wrap, which may ease application of the pressure wrap and/or speed application time. Discrete regions of hooks 34 are illustrated as round dots, or "coins," of hooks 34 that are positioned on second side 26 of elongated elastic strap 12, though various examples of pressure wrap 10 may include discrete regions of hooks 34 of any suitable size and/or shape that may be included on first side 24 and/or second side 26 of elongated elastic strap 12. While examples herein are generally described as being hooks within the discrete regions of hooks 34, alternate embodiments wherein one or more discrete regions include pile for hook-and-loop fasteners instead of hooks also are within the scope of the present disclosure.

Securement 16 of pressure wrap 10 is configured to selectively and removably secure distal end 22 of elongated elastic strap 12 to an intermediate portion of elongated elastic strap 12, thereby securing pressure wrap 10 with respect to the subject. Said intermediate portion is positioned between proximal end 20 and distal end 22, with securement 16 being configured to maintain pressure wrap 10 in position after it is applied to the subject. The intermediate portion of elongated elastic strap 12 can be any portion of elongated elastic strap 12 that has already been wrapped around the subject in a previous loop. Securement 16 may be positioned at or near distal end 22 of elongated elastic strap 12, or at another location along elongated elastic strap 12. Securement 16 may include a manipulatable fastener 36 that is hand-operated to secure distal end 22 of elongated elastic strap 12 to the intermediate portion of elongated elastic strap 12. Additionally or alternatively, securement 16 may include an automatic fastener 38 that is configured to automatically secure distal end 22 of elongated elastic strap 12 to the intermediate portion when automatic fastener 38 contacts the intermediate portion of elongated elastic strap 12. In some examples, manipulatable fastener 36 is configured to be a redundant fastener.

Examples of automatic fastener 38 include hooks to engage pile 28 of elongated elastic strap 12, adhesives, and/or magnets. Other types of automatic fasteners 38 also are within the scope of the present disclosure. In a specific example, automatic fastener 38 may be a pull-tab 48 coupled to elongated elastic strap 12, such as to distal end 22 of elongated elastic strap 12. Said pull-tab 48 may include hooks on one or both sides to engage pile 28 of elongated elastic strap 12 when the two are brought into contact with one another. In one example, pull-tab 48 includes hooks on just one side of pull-tab 48 (e.g., on a second fastener side 58 of automatic fastener 38, which may be arranged parallel to second side 26 of elongated elastic strap 12). Additionally or alternatively, automatic fastener 38 (e.g., pull-tab 48) may include a label 52 configured to receive information, such as a time at which the pressure wrap is applied to the subject, the identity of the user who applied the pressure wrap to the subject, and/or details regarding the subject's wound, physical or mental condition, etc. In a specific example, label 52 may be positioned on a first fastener side 60 of automatic fastener 38, which may be parallel to first side 24 of elongated elastic strap 12.

Examples of manipulatable fastener 36 include safety pins, other types of pins, clips, hooks, snaps, ties, clasps, and/or buttons, and generally require some manual manipulation by the user to secure. Manipulatable fastener 36 may be coupled to automatic fastener 38. For example, manipulatable fastener 36 may be a safety pin that is pinned to pull-tab 48. Additionally or alternatively, manipulatable fastener 36 may be coupled to elongated elastic strap 12, such as to distal end 22 of elongated elastic strap 12. In some examples, manipulatable fastener 36 is configured for redundant, or backup, securing of the pressure wrap. For example, automatic fastener 38 may be sufficient to secure distal end 22 of elongated elastic strap 12 once pressure wrap 10 is applied to a subject, with manipulatable fastener 36 being secured (e.g., pinned to elongated elastic strap 12, in the case of a safety pin) if desired.

Pressure wrap 10 has a resting configuration (as shown, for example, in FIG. 7) and an applied configuration (as shown, for example, in FIG. 6), with elongated elastic strap 12 being under tension when pressure wrap 10 is in the applied configuration, such as when applied to a subject. A length of elongated elastic strap 12 when pressure wrap 10 is in the resting configuration (its "resting length") is at most the length of elongated elastic strap 12 when pressure wrap 10 is in the applied configuration (its "stretched length"). For example, the stretched length may be at least 40% greater than the resting length, at least 50% greater than the resting length, at least 60% greater than the resting length, at least 70% greater than the resting length, at least 80% greater than the resting length, at least 90% greater than the resting length, and/or at least 100% greater than the resting length. In illustrative examples, length 18 of elongated elastic strap 12 in the resting configuration may be at least 1 foot, at least 1.5 feet, at least 2 feet, at least 2.5 feet, at least 3 feet, at least 3.5 feet, at least 4 feet, at least 4.5 feet, at least 5 feet, at least 5.5 feet, at least 6 feet, at least 6.5 feet, at least 7 feet, at least 7.5 feet, and/or at least 8 feet, while length 18 of elongated elastic strap 12 in the applied configuration may be at least 2 feet, at least 3 feet, at least 4 feet, at least 5 feet, at least 6 feet, at least 7 feet, at least 8 feet, at least 9 feet, at least 10 feet, at least 11 feet, at least 12 feet, at least 13 feet, at least 14 feet, at least 15 feet, and/or at least 16 feet. In illustrative examples, strap width 40 of elongated elastic strap 12 may be at least 0.75 inches, at least 1 inch, at least 1.5 inches, at least 2 inches, at least 3 inches, at most 1 inch, at most 1.1 inches, at most 1.2 inches, at most 1.3 inches, at most 1.4 inches, at most 1.5 inches, at most 1.6 inches, at most 1.7 inches, at most 1.8 inches, at most 1.9 inches, at most 2 inches, at most 2.5 inches, at most 3 inches, at most 4 inches, and/or at most 5 inches. The elasticity of elongated elastic strap 12 may facilitate maintaining tension as pressure wrap 10 is applied to a subject.

Figure 6:
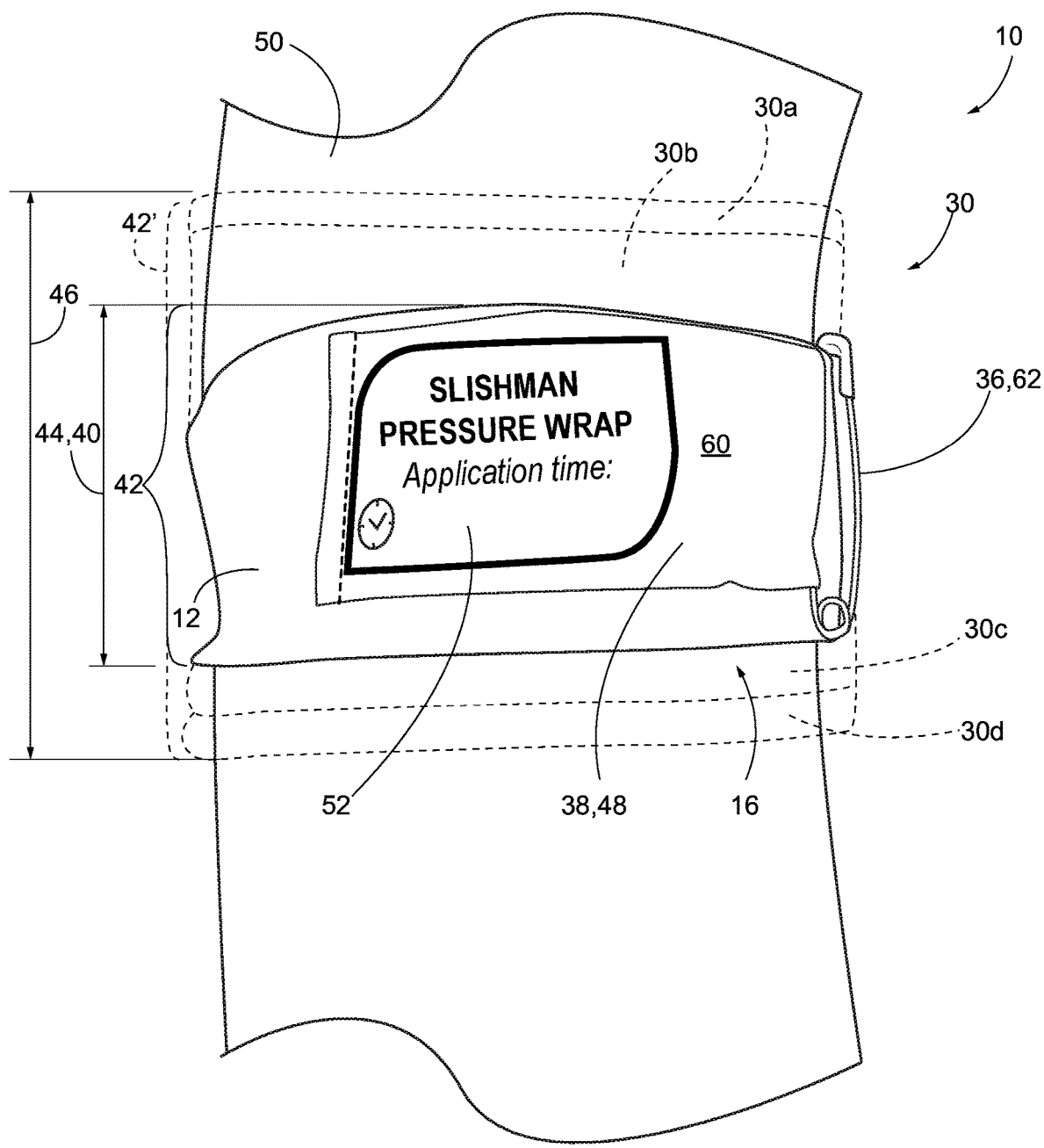
FIG. 6 shows an example of a distal end of a pressure wrap.

In the applied configuration, pressure wrap 10 applies a pressure to the subject. For example, when applied to a subject's arm, pressure wrap 10 exerts a pressure on the subject's arm as a result of tension applied to elongated elastic strap 12 as the plurality of loops are formed around the subject's arm. Depending on the relative placement of the plurality of loops formed with elongated elastic strap 12, the pressure may be applied to the subject in a relatively narrow area, which may be referred to herein as a compression zone 42. For example, FIG. 6 illustrates an example of pressure wrap 10 applied to a subject's arm 50. As shown in solid lines, if each subsequent loop of plurality of loops 30 of elongated elastic strap 12 is sequentially stacked on top of (i.e., overlapping and/or covering) previous loops (forming at least substantially concentric loops), the pressure applied by pressure wrap 10 may be relatively concentrated in the area where the loops are placed, such that a width 44 of compression zone 42 may be approximately the same width as strap width 40 of elongated elastic strap 12. Alternatively, if one or more loops of plurality of loops 30 either only partially overlap previous loops, or do not overlap previous loops, the pressure applied by pressure wrap 10 may be distributed over a larger area of the subject, and thus may be said to have a wider compression zone. In this manner, compression zone 42 may be expanded with each incremental loop formed with elongated elastic strap 12. For example, as shown in dashed line in FIG. 6, loops 30*a*, 30*b*, 30*c*, and 30*d* are disbursed such that they only partially overlap one or more other loops of plurality of loops 30, thereby creating a compression zone 42' having a width 46 that is larger than width 44, thereby distributing the pressure applied by pressure wrap 10 over a larger area of subject's arm 50. In other words, pressure wrap 10 may be configured to be applied to the subject such that each loop of the plurality of loops 30 may be positioned to spread and/or distribute the pressure applied by pressure wrap 10. Thus, while conventional tourniquets have a fixed width, presently disclosed pressure wraps 10 can apply pressure over a selectively adjustable compression zone 42, which may be selectively positioned with respect to the wound site.

With continued reference to FIG. 1, the pressure applied by pressure wrap 10 may be selectively and/or continuously varied, or adjusted, based on the tension applied to elongated elastic strap 12 as it is wrapped around a subject, based on the number of loops formed around the subject, and/or based on the width of the compression zone due to the disbursement of the plurality of loops as the loops are formed around the subject. In an example, the tension applied to elongated elastic strap 12 may be selectively adjusted independently for each loop of the plurality of loops formed around the subject. As another example, the width of the compression zone may be expanded with each incremental loop of the plurality of loops as the pressure wrap is applied to the subject.

In this manner, pressure wrap 10 may be applied to a subject such that pressure wrap 10 exerts a pressure on the subject that is sufficient to stop bleeding at a wound site (e.g., by applying direct pressure to the wound, such that the compression zone overlaps or at least partially covers the wound site). Additionally or alternatively, pressure wrap 10 may be applied to a subject such that pressure wrap 10 exerts a pressure on the subject that is sufficient to at least partially occlude blood flow distal to pressure wrap 10. When pressure wrap 10 is used to occlude blood flow distal to a wound site or distal to the location at which pressure wrap 10 is applied to the subject, pressure wrap 10 may be applied to the subject such that the compression zone is proximal to the wound site.

As disclosed herein, pressure wraps 10 may be configured to improve ease and/or speed of application, as compared to prior art wraps and tourniquets. When treating a wound, it may be critical to apply pressure (e.g., wraps or tourniquets) as fast as possible to limit bleeding. However, the speed of application may be affected by the ease of application of the particular wrap or tourniquet. Speed of application also may be impacted by the dexterity of the injured party, as well as the rescuer. Simplicity may be particularly advantageous when the injured party is forced to attempt one-handed application to himself/herself. Thus, disclosed pressure wraps 10 may be configured such that they may be applied without requiring fine motor movements, such as via reliance on automatic fastener 38 of securement 16 and/or discrete regions of hooks 34. Additionally or alternatively, disclosed pressure wraps 10 may be configured such that they may be applied with any orientation of elongated elastic strap 12 with respect to the subject. Pressure wraps 10 generally are configured to be simple to apply to a subject, and pressure wraps 10 may require little to no training.

Once bleeding from a wound site is controlled, alleviating pain from the wound, pain from progressively worsening limb ischemia, and/or pain from the tourniquet or wrap itself becomes a higher priority. However, conventional tourniquets do not provide for a slow or controlled removal, or conversion. For example, once the ratcheting system is released on a windlass tourniquet, the pressure is essentially immediately and entirely removed. Pressure wrap 10, however, may be configured such that the pressure applied by pressure wrap 10 may be selectively decreased by incrementally unwrapping one or more loops of the plurality of loops 30, after pressure wrap 10 has been applied to the subject. In other words, pressure wrap 10 may be gradually removed from a subject without immediately releasing all the pressure applied by pressure wrap 10 at once. In an example, elongated elastic strap 12 may be wrapped around a subject's arm such that eight loops are formed around the arm. To selectively reduce the amount of pressure applied by pressure wrap 10, the eight loops may be incrementally unwrapped, one at a time, with the underlying loops remaining intact and applying pressure to the subject, held in place by the plurality of discrete regions of hooks 34 spaced along elongated elastic strap 12. While said discrete regions of hooks 34 may allow for this selective adjustment of the pressure applied by pressure wrap 10, the plurality of discrete regions of hooks 34 also may be configured to inhibit or prevent an unintentional reduction in the pressure applied by pressure wrap 10 during application of the pressure wrap to a subject (e.g., by inhibiting or preventing unintentional unrolling or unwrapping of the plurality of loops). In other words, the coupling provided between pile 28 of elongated elastic strap 12 and discrete regions of hooks 34 may be sufficient to retain a given segment of elongated elastic strap 12 in place against the previous loop of the plurality of loops, while at the same time being not so great as to prevent selective incremental unwrapping of one or more loops of the plurality of loops formed with elongated elastic strap 12.

Adjustment component 32 generally may include any component or mechanism that permits selective adjustment of the size of adjustable loop 14. In some examples, adjustment component 32 may be configured to facilitate one-handed application of pressure wrap 10 to the subject, including one-handed adjustment of adjustable loop 14. In some cases, adjustment component 32 is removably coupled to elongated elastic strap 12. Examples of adjustment component 32 may include a buckle 54 or a sleeve 100, and specific examples of which will be described in more detail herein.

Pressure wrap 10 may be configured such that first side 24 of elongated elastic strap 12 is configured to be positioned facing the subject when pressure wrap 10 is applied to the subject, for at least adjustable loop 14. In specific examples, pressure wrap 10 may be configured such that second side 26 of elongated elastic strap 12 does not contact the subject when pressure wrap 10 is applied to the subject. While pressure wrap 10 is generally configured to function to apply sufficient pressure to a wound regardless of which side of elongated elastic strap 12 contacts the subject, it may be more comfortable to the subject to avoid having any components with hooks (e.g., discrete regions of hooks 34 and/or automatic fastener 38 of securement 16) contacting the subject. In other words, pressure wrap 10 may be configured to apply pressure to the subject regardless of whether first side 24 or second side 26 of elongated elastic strap 12 faces the subject when pressure wrap 10 is applied to the subject, though the pressure wrap may be designed to avoid said contact between the subject and any hooks of pressure wrap 10, if desired. Similarly, pressure wrap 10 may be configured to avoid contact between adjustment component 32 and the subject. For example, adjustment component 32 may be coupled to second side 26 of elongated elastic strap 12, with the elongated elastic strap 12 being configured such that second side 26 does not contact the subject, at least for adjustable loop 14 (or the first loop of the plurality of loops 30).

Pressure wraps 10 may be provided with a carrying pouch or case that is configured to store pressure wrap 10 when not in use. Pressure wraps 10 generally are compact in size, such as for increased portability. Pressure wraps 10 also may be relatively inexpensive, which may increase their availability in the field. Various examples of pressure wraps 10 may be configured to apply pressure to pediatric, adult, and/or animal subjects. As described herein, pressure wrap 10 may be utilized to apply direct pressure to a wound site of a subject and/or may be utilized as a tourniquet that occludes blood flow distal to a wound site. Various examples of pressure wrap 10 may be configured to be one-size-fits-all. Pressure wraps 10 may be configured for single-use, or may be configured for multiple uses. In some cases, just a portion of pressure wrap 10 may be configured for multiple uses. For example, elongated elastic strap 12 may be configured for single use, while adjustment component 32 may be configured to be used multiple times (e.g., after sterilization, such as in an autoclave). Presently disclosed pressure wraps 10 may have multiple uses in addition to applying pressure to a subject. For example, disclosed pressure wraps 10 may have utility as a shoulder sling, a swathe, a belt, a knee wrap, an ankle wrap, a saline bottle pressure applicator, and/or a roof rack tie down.

Figure 2:
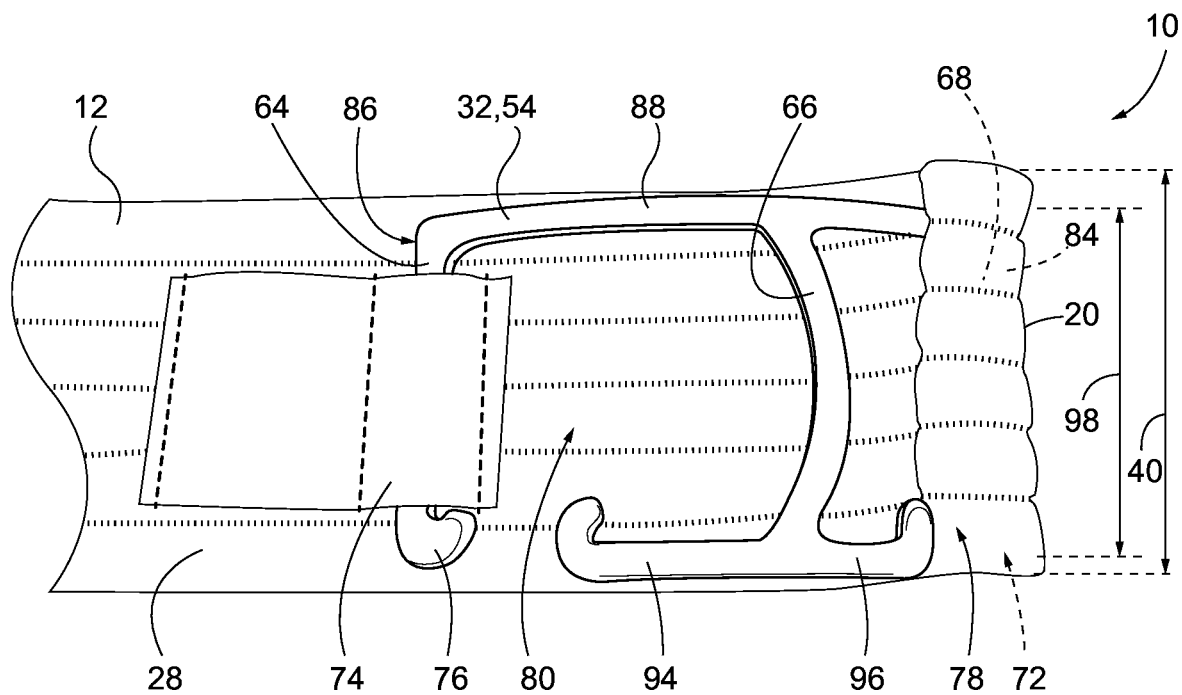
FIG. 2 is a top plan view of a portion of an example of a pressure wrap.
Figure 3:
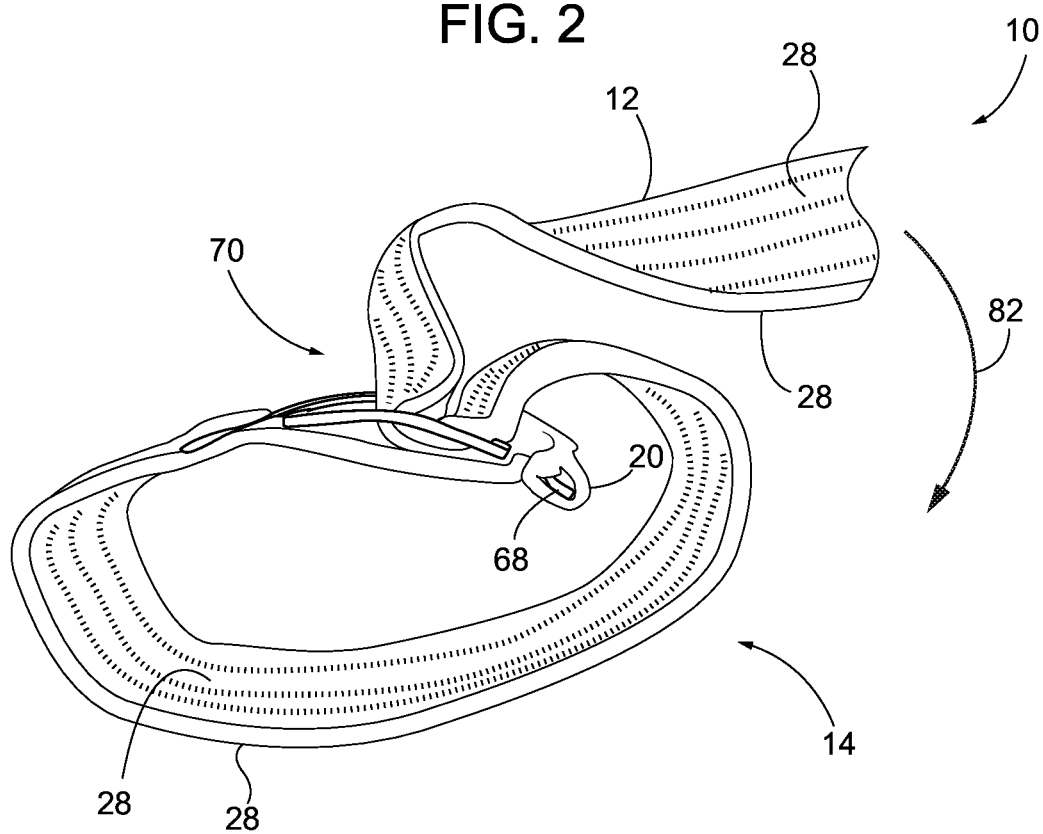
FIG. 3 is a side elevation view of an example of a pressure wrap, with an initial adjustable loop formed.

Examples of pressure wraps 10 (and/or components thereof) will now be described with reference to FIGS. 2-16. FIGS. 2-5 illustrate an example of pressure wrap 10 having buckle 54 as its adjustment component 32. FIG. 2 provides a detail view of proximal end 20 of elongated elastic strap 12, showing engagement between buckle 54 and elongated elastic strap 12. FIG. 3 illustrates adjustable loop 14 formed in elongated elastic strap 12, with FIG. 4 illustrating the same thing from a different angle to better show how elongated elastic strap 12 may be threaded through buckle 54. FIG. 5 illustrates pressure wrap 10 with a plurality of loops 30 formed therein, with adjustable loop 14 forming the inner-most loop, or first loop, of plurality of loops 30. FIG. 5 also illustrates securement 16 in the form of pull-tab 48 (which is an example of automatic fastener 38) and a safety pin 62 (which is an example of manipulatable fastener 36).

Buckle 54 may include an anchor bar 64, a slider bar 66, and/or a push bar 68. Anchor bar 64 may be configured to anchor buckle 54 to elongated elastic strap 12, optionally such that buckle 54 is removably coupled to elongated elastic strap 12. For example, as best seen in FIGS. 2 and 4, elongated elastic strap 12 may include an anchor slot 74 that receives anchor bar 64. In some examples, anchor slot 74 may be coupled to elongated elastic strap 12 and may include hooks configured to engage pile 28 of elongated elastic strap 12. As shown in FIGS. 2 and 4, anchor slot 74 may extend at least substantially transverse to length 18 of elongated elastic strap 12. To engage anchor slot 74, anchor bar 64 simply may be inserted through anchor slot 74 by sliding anchor bar 64 therethrough. Anchor bar 64 may include a J-bend 76 configured to prevent or inhibit unintentional removal of anchor bar 64 from anchor slot 74. For example, J-bend 76 may catch onto anchor slot 74 to retain anchor bar 64 within anchor slot 74.

Slider bar 66, which is generally positioned between anchor bar 64 and push bar 68, may be configured to engage elongated elastic strap 12 and create a direction change 70 (FIGS. 3-4) therein, such that adjustable loop 14 is formed when elongated elastic strap 12 is engaged with slider bar 66 to create direction change 70 therein. For example, to form adjustable loop 14, a portion 77 of elongated elastic strap 12 may be positioned within a first space 78 of buckle 54, between push bar 68 and slider bar 66. Said portion 77 of elongated elastic strap 12 may then be fed through a second space 80 of buckle 54, between slider bar 66 and anchor bar 64, and wrapped partially around slider bar 66 to form direction change 70 in elongated elastic strap 12. Elongated elastic strap 12 may then continue to be wrapped around adjustable loop 14 (following direction arrow 82) to form the plurality of loops 30 around adjustable loop 14, as shown in FIG. 5. When elongated elastic strap 12 is wrapped around adjustable loop 14 to the point that elongated elastic strap 12 reaches anchor slot 74 (e.g., at the completion of the loop of plurality of loops 30 subsequent to adjustable loop 14), pile 28 of elongated elastic strap 12 may engage hooks of anchor slot 74 to at least partially secure that loop as elongated elastic strap 12 is continued to be wrapped to form additional subsequent loops of plurality of loops 30.

Push bar 68 may be engaged with proximal end 20 of elongated elastic strap 12, with push bar 68 being configured to inhibit pinching or pulling of the subject's skin as pressure wrap 10 is applied to the subject. In some examples, push bar 68 may be selectively removable from a pocket 72 formed in proximal end 20 of elongated elastic strap 12. In this manner, push bar 68 may be at least substantially obscured, or covered, by proximal end 20 of elongated elastic strap 12 when push bar 68 is positioned in pocket 72, as best seen in FIGS. 2-3.

Figure 9:
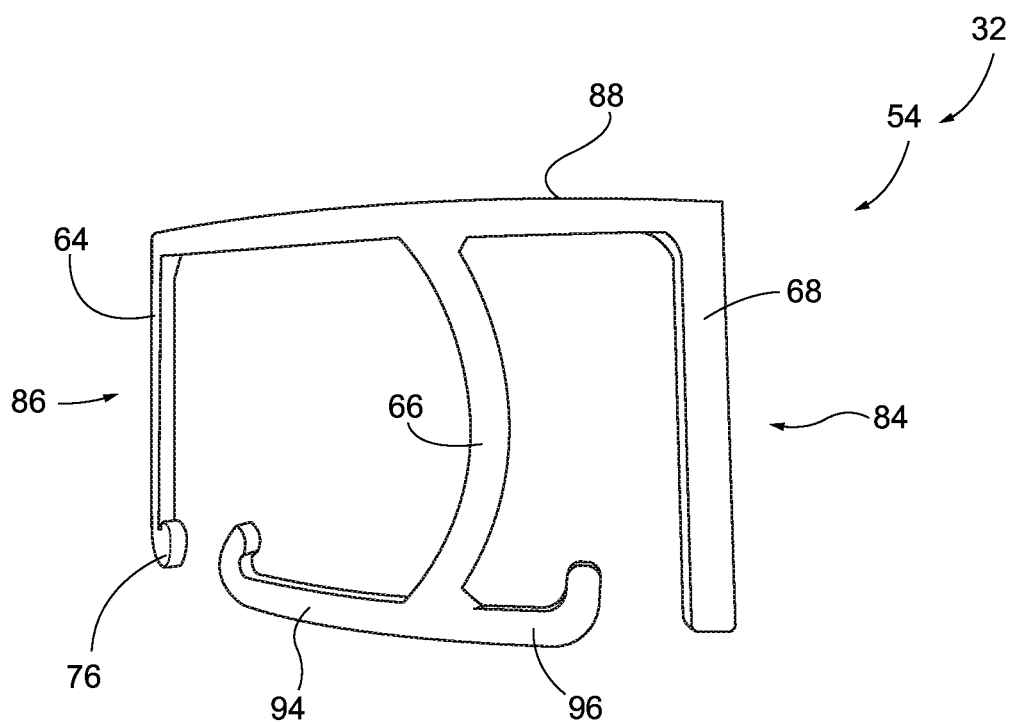
FIG. 9 shows a top plan view of an example of a buckle that may be used with pressure wraps according to the present disclosure.
Figure 10:
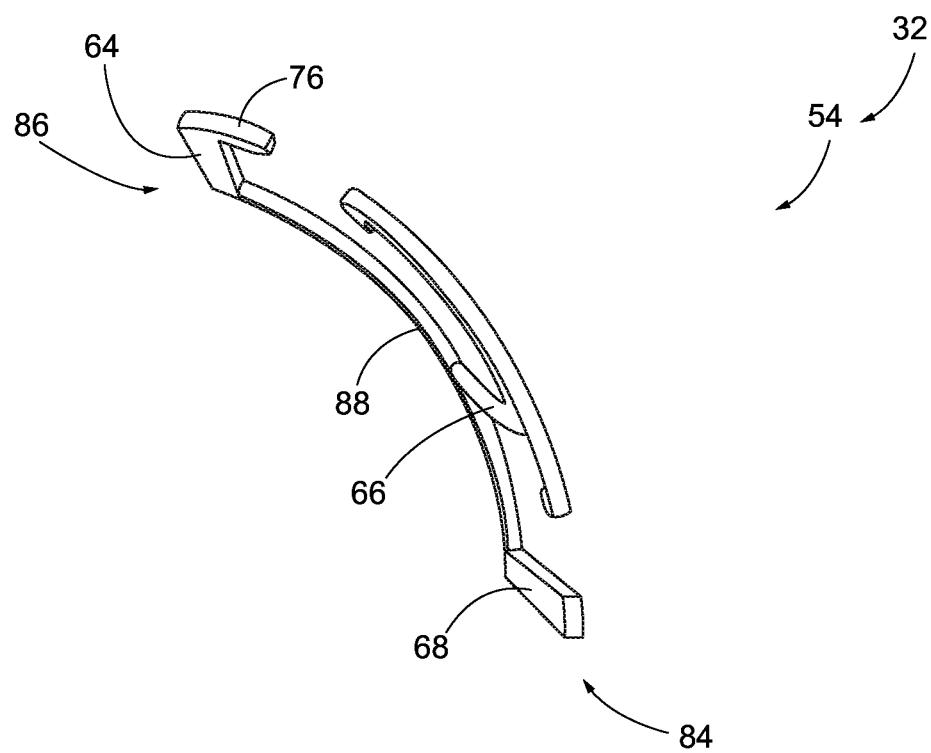
FIG. 10 is a side perspective view of the buckle of FIG. 9.

With reference to FIG. 2 and FIGS. 9-10 (FIGS. 9-10 illustrate an example of buckle 54 apart from pressure wrap 10), buckle 54 may be described as having a proximal buckle end 84 and a distal buckle end 86, with an elongated member 88 extending therebetween. Push bar 68, slider bar 66, and anchor bar 64 all may extend from elongated member 88, as shown in the Figures. Proximal buckle end 84 may be defined by push bar 68 and coupled to proximal end 20 of elongated elastic strap 12. Distal buckle end 86 may be defined by anchor bar 64. Anchor bar 64 and push bar 68 may be substantially parallel to one another. Additionally or alternatively, anchor bar 64 and/or push bar 68 may be arranged at least substantially perpendicularly to elongated member 88. Said elongated member 88 may be substantially parallel to length 18 of elongated elastic strap 12 when buckle 54 is engaged with elongated elastic strap 12, and thus anchor bar 64 and push bar 68 may be oriented substantially perpendicularly to length 18 of elongated elastic strap 12 when buckle 54 is engaged with elongated elastic strap 12. Slider bar 66 is illustrated as being curved, which may encourage engagement with elongated elastic strap 12, though other arrangements of slider bar 66 also are within the scope of the present disclosure. In other words, slider bar 66 may be configured to retain elongated elastic strap 12 about slider bar 66 and assist in forming adjustable loop 14. For example, slider bar 66 may include an upper catch 94 (which additionally or alternatively may be described as an upper tab, or upper protrusion) that extends from slider bar 66 towards anchor bar 64, with upper catch 94 being configured to retain elongated elastic strap 12 in second space 80 between slider bar 66 and anchor bar 64. Additionally or alternatively, slider bar 66 may include a lower catch 96 (which additionally or alternatively may be described as a lower tab, or lower protrusion) that extends from slider bar 66 towards push bar 68, with lower catch 96 being configured to retain elongated elastic strap 12 in first space 78 of buckle 54 between slider bar 66 and push bar 68. In some pressure wraps 10, buckle 54 may have a buckle width 98, which may be at most strap width 40 of elongated elastic strap 12, as illustrated in FIG. 2. In other examples, buckle width 98 may be substantially equal to strap width 40, or buckle width 98 may be greater than strap width 40.

When elongated elastic strap 12 is threaded through buckle 54 to form adjustable loop 14, as described and/or illustrated herein, a user may selectively tighten, or reduce the size of adjustable loop 14, by pulling on elongated elastic strap 12 at a location distal to portion 77 of elongated elastic strap 12 that is engaged with buckle 54. Similarly, to selectively loosen, or increase the size of adjustable loop 14, elongated elastic strap 12 may be threaded through buckle 54 in the opposite direction.

Buckle 54 (or other adjustment component 32) may be formed of any suitable material. In some examples, buckle 54 may be formed of stainless steel or a polymer material. In general, buckle 54 may be formed of a lightweight material that may be configured to resiliently deform during application of pressure wrap 10. In some examples, buckle 54 may be contoured to conform to the subject. For example, as shown in FIG. 10, buckle 54 may be curved to be complementary to a subject's limb. In some examples, buckle 54 may be configured to be plastically deformed, bent, or shaped, to increase conformity to the subject, while still being strong enough to secure elongated elastic strap 12 with enough tension to apply the desired pressure to the subject's limb. Buckle 54 may be formed, for example, by additive manufacturing (e.g., 3D printing), stamping, molding, and/or any other suitable technique. In some examples, buckle 54 may be intentionally burred, abraded, and/or not smoothed, which may improve the engagement between buckle 54 and elongated elastic strap 12. In other examples, buckle 54 may be smoothed to facilitate movement of elongated elastic strap 12 with respect to buckle 54, such as to facilitate cinching or tightening of adjustable loop 14.

Figure 11:
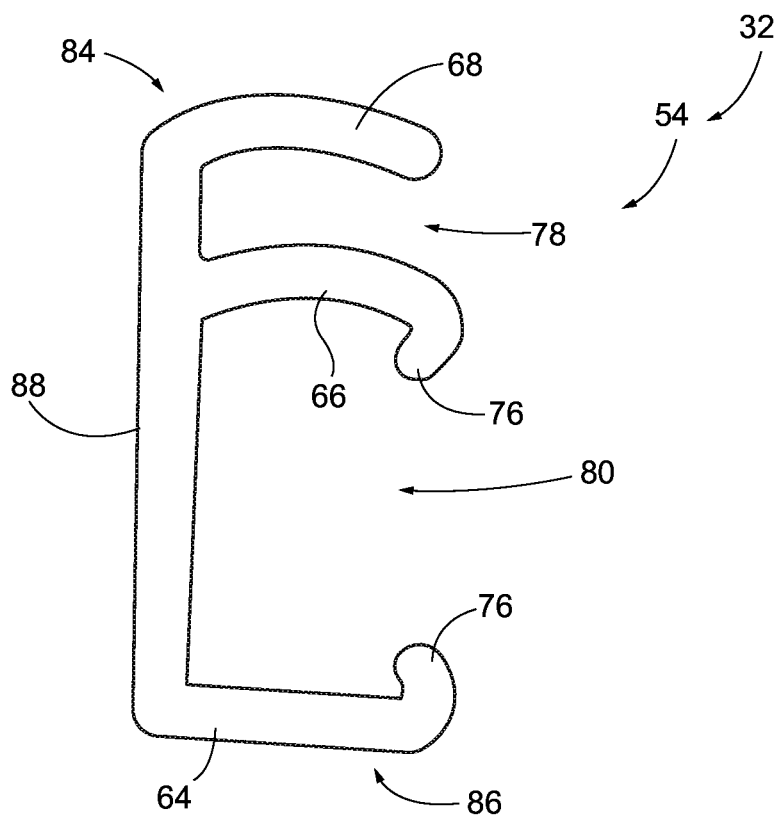
FIG. 11 is a top plan view of another example of a buckle that may be used with the presently disclosed pressure wraps.

FIGS. 11-14 show other examples of buckle 54 for illustrative purposes, though many different shapes and arrangements of buckles 54 are within the scope of the present disclosure, and buckles 54 are not limited to the specific examples illustrated herein. For example, FIG. 11 illustrates an example of buckle 54 similar to the example shown in FIG. 9, having anchor bar 64, slider bar 66, and push bar 68, though said bars may be shorter, longer, angled differently, and/or shaped differently in various examples of buckle 54. Buckle 54 in FIG. 11 does not include upper catch 94, which may result in a larger second space 80 between anchor bar 64 and slider bar 66. Similarly, buckle 54 in FIG. 11 does not include lower catch 96. Slider bar 66 may be positioned further away or closer to anchor bar 64 or push bar 68 in various examples of buckle 54. Additionally or alternatively, push bar 68 may be spaced away from proximal buckle end 84, and/or anchor bar 64 may be spaced away from distal buckle end 86 in various examples of buckle 54. Anchor bar 64, slider bar 66, and/or push bar 68 each may include one or more J-bends 76, in various examples of buckle 54.

Figure 12:
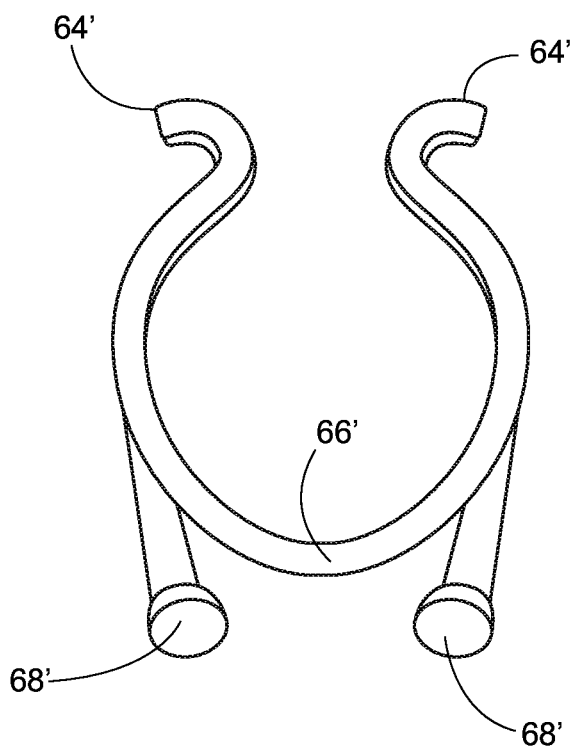
FIG. 12 is a top plan view of another example of a buckle that may be used with the presently disclosed pressure wraps.
Figure 13:
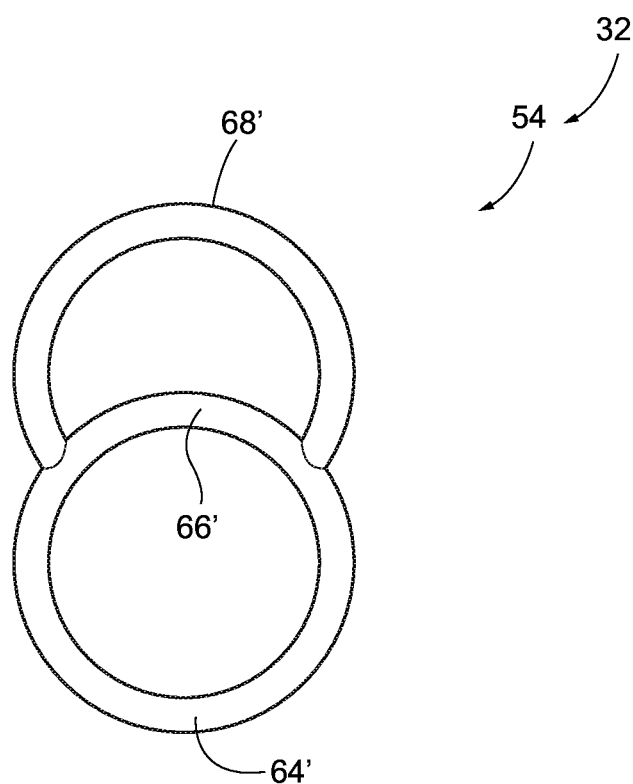
FIG. 13 is a top plan view of another example of a buckle that may be used with the presently disclosed pressure wraps.
Figure 14:
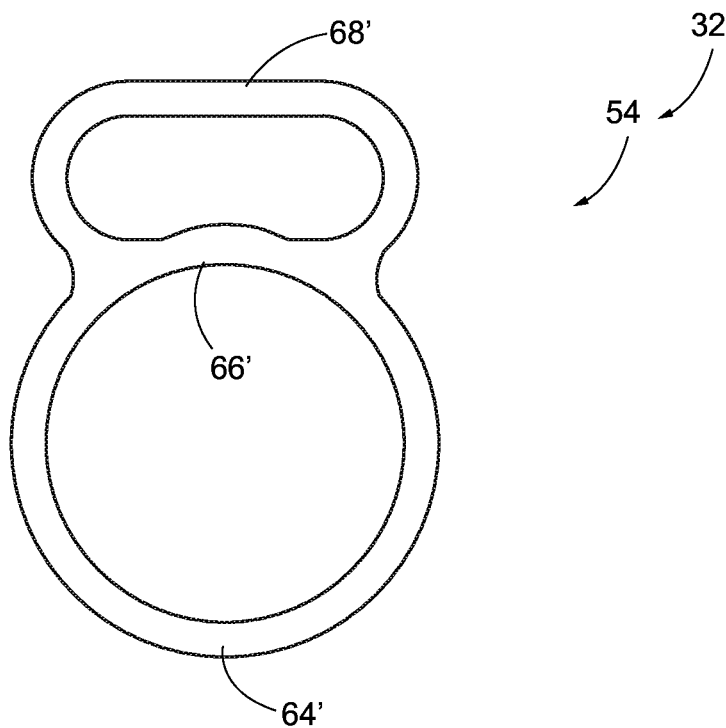
FIG. 14 is a top plan view of another example of a buckle that may be used with the presently disclosed pressure wraps.

FIGS. 12-14 illustrate different examples of buckle 54, which may or may not include structures similar to anchor bar 64, slider bar 66, and/or push bar 68, though they still may perform similar functions as described herein. For example, buckle 54 shown in FIG. 12 may include anchor portions 64' for anchoring buckle 54 to elongated elastic strap 12, and push portions 68' for inhibiting pinching or pulling of the subject's skin while the pressure wrap is tightened around the subject. Elongated elastic strap 12 may be formed into an adjustable loop by engaging and wrapping around slider portion 66'. Similarly, examples of buckles 54 in FIGS. 13-14 may include anchor portions 64' for anchoring buckle 54 to elongated elastic strap 12, slider portions 66' for engaging elongated elastic strap 12 to form adjustable loop 14, and push portions 68' for preventing or inhibiting pinching or pulling of the subject's skin during application of pressure wrap 10.

Figure 15:
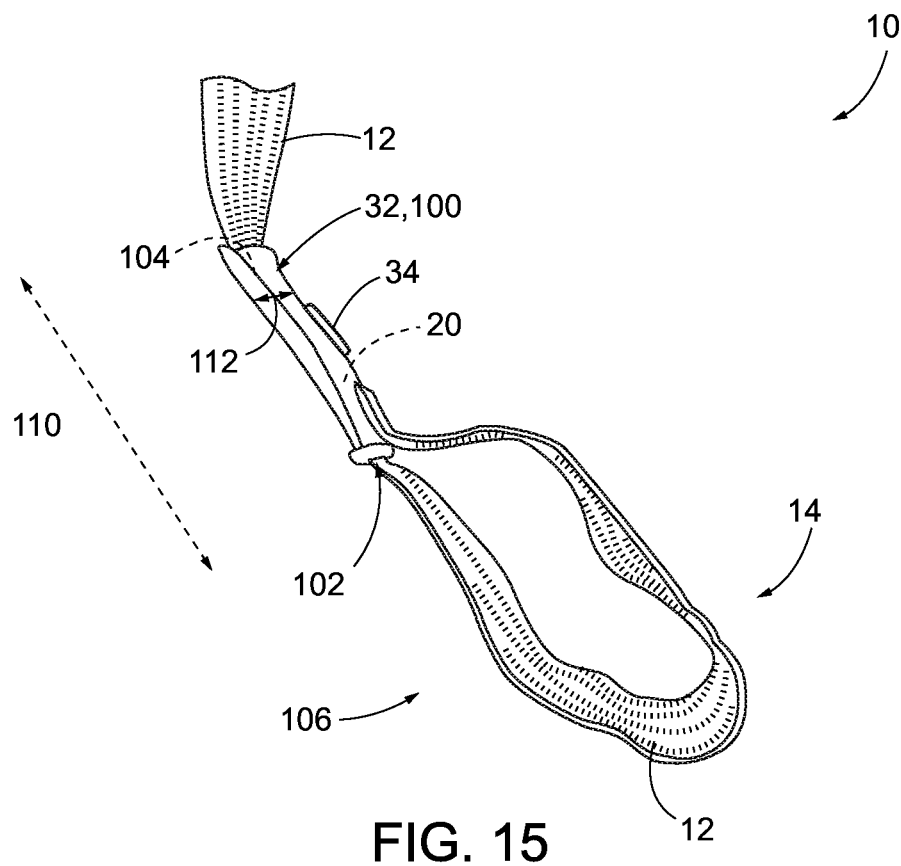
FIG. 15 is a side elevation view of another example of a pressure wrap according to the present disclosure, having an adjustment component in the form of a sleeve for forming the initial adjustable loop.
Figure 16:
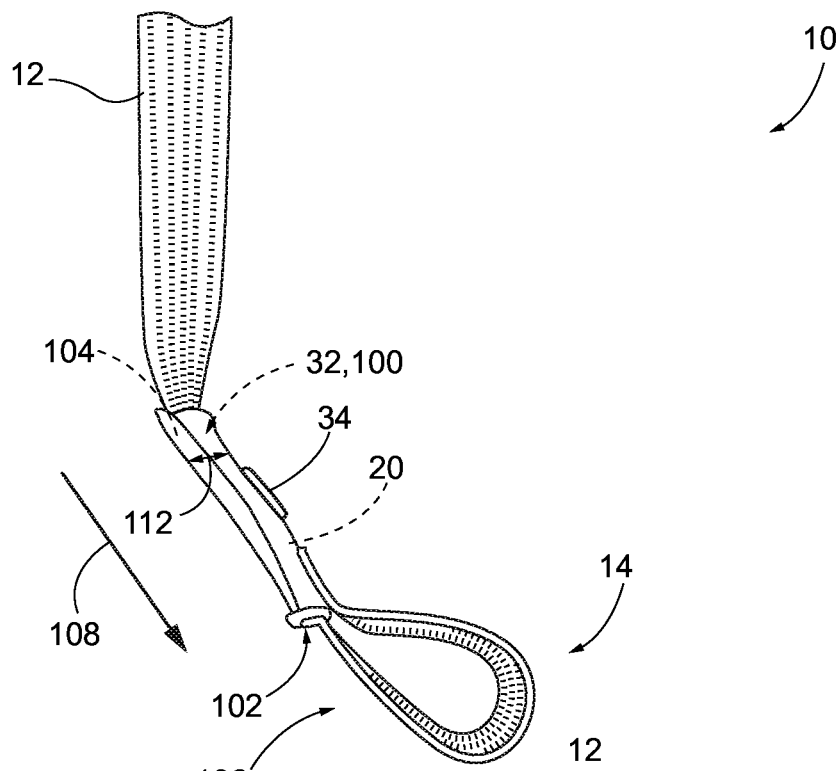
FIG. 16 is a side elevation view of the pressure wrap of FIG. 15, illustrating the adjustability of the size of the initial adjustable loop via sliding the sleeve along the strap.

In other examples of pressure wrap 10, and with reference to FIGS. 15-16, adjustment component 32 may be, and/or may include, a sleeve 100 coupled to elongated elastic strap 12. Said sleeve 100 defines a passage 102 through which elongated elastic strap 12 is free to longitudinally translate prior to forming the plurality of loops 30. Proximal end 20 of elongated elastic strap 12 may be coupled to an interior surface 104 of sleeve 100 (e.g., within passage 102), and adjustable loop 14 may be formed by positioning a length 106 of elongated elastic strap 12 proximal to sleeve 100, with distal end 22 of elongated elastic strap 12 being positioned distal to sleeve 100. The size of adjustable loop 14 may be selectively adjusted by sliding elongated elastic strap 12 through sleeve 100 to increase or decrease length 106 of elongated elastic strap 12 positioned proximal to sleeve 100, thereby adjusting the size of adjustable loop 14. For example, the size of adjustable loop 14 may be selectively decreased by translating elongated elastic strap 12 with respect to sleeve 100 (e.g., along arrow 108) such that distal end 22 of elongated elastic strap 12 is moved further away from sleeve 100. Similarly, the size of adjustable loop 14 may be selectively increased by translating elongated elastic strap 12 with respect to sleeve 100 (e.g., along arrow 108) such that distal end 22 of elongated elastic strap 12 moves closer to sleeve 100.

In some examples, sleeve 100 may be a tubular sleeve, with a diameter 112 of sleeve 100 being transverse to length 18 of elongated elastic strap 12. A longitudinal axis 110 of sleeve 100 may be at least substantially parallel to length 18 of elongated elastic strap 12. Sleeve 100 may include gauze or other absorbent material coupled within passage 102 and/or to the outside of sleeve 100. Additionally or alternatively, sleeve 100 may include one or more discrete regions of hooks 34 that are compatible with pile 28 of elongated elastic strap 12, with said hooks 34 optionally being positioned on one or both sides of sleeve 100. In this manner, as subsequent loops of elongated elastic strap 12 are formed and wrapped around sleeve 100 and adjustable loop 14 as pressure wrap 10 is applied to a subject, a portion of elongated elastic strap 12 brought into contact with a discrete region of hooks 34 on sleeve 100 may be retained in place to help prevent unintentional unwrapping or reduction in pressure applied by pressure wrap 10. Sleeve 100 may be any suitable material, including but not limited to flexible fabric materials, elastic materials, and/or webbing.

Figure 8:
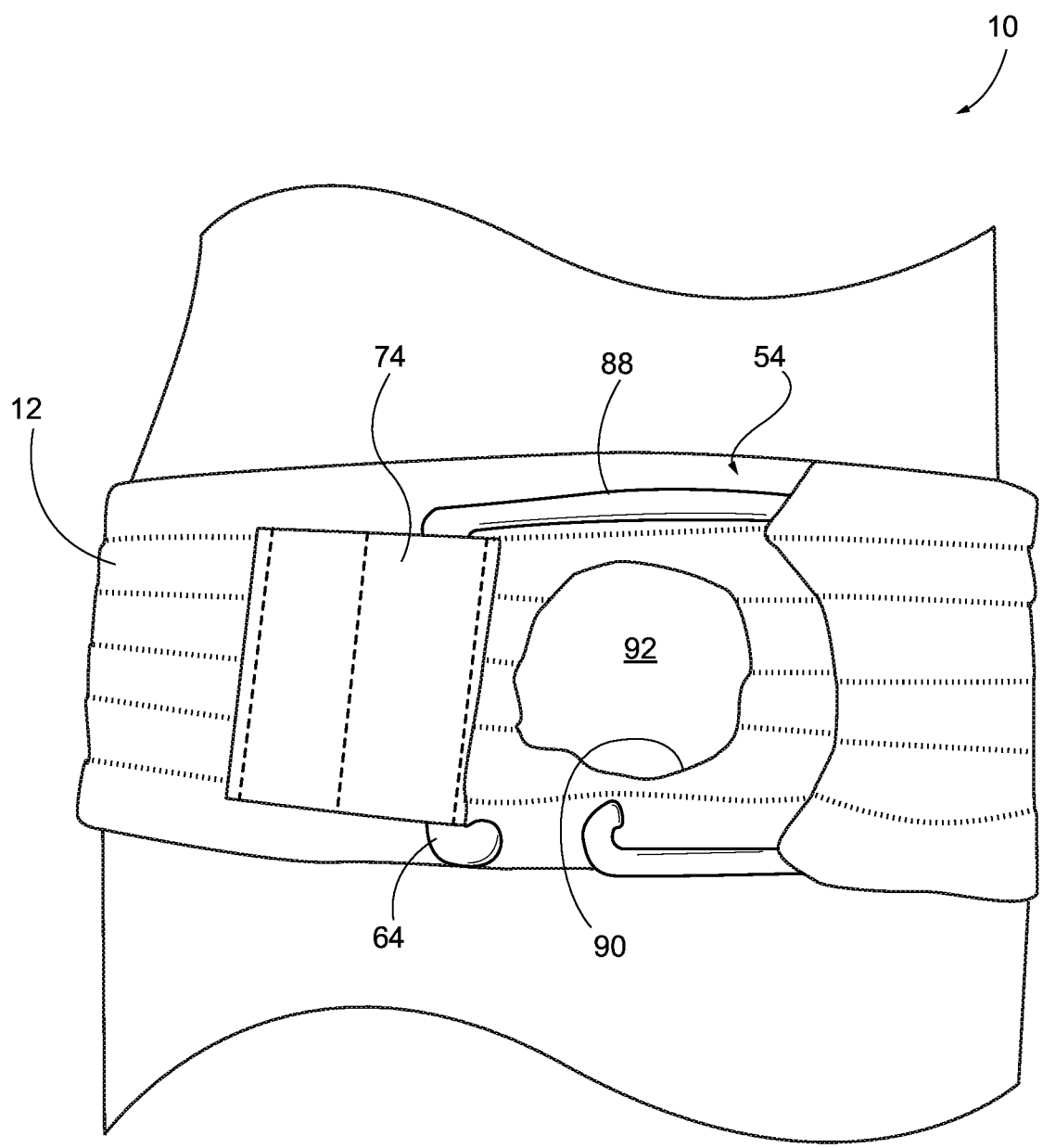
FIG. 8 shows an example of a pressure wrap having a visualization window formed therein.

FIG. 8 illustrates another example of pressure wrap 10, which includes a visualization window 90 formed in elongated elastic strap 12. Visualization window 90 may be configured to allow viewing of a wound site 92 of the subject as pressure wrap 10 is applied to the subject. Visualization window 90 may permit a user or the subject to monitor the wound site, clean the wound site, treat the wound site, stitch or repair the wound site, irrigate the wound site, apply a hemostatic agent, apply a hard material for more focused pressure directly over the wound, and/or may permit access to the subject, such as to insert a catheter, IV line, or the like, all while maintaining compression on the subject. Additionally or alternatively, embodiments of pressure wraps 10 disclosed herein may include gauze, absorptive material, and/or absorptive or non-absorptive wound dressings, which may be configured to increase comfort for the subject, absorb blood from wound site 92, and/or facilitate occlusion during application of pressure wrap 10. For example, pressure wrap 10 may include gauze or other absorptive material along elongated elastic strap 12, at one or more discrete locations along elongated elastic strap 12, adjacent proximal end 20 of elongated elastic strap 12, adjacent distal end 22 of elongated elastic strap 12, along adjustable loop 14, and/or adjacent adjustment component 32. Additionally or alternatively, elongated elastic strap 12 may be compatible with typical fasteners used with such gauzes, absorptive materials/wound dressing, and/or non-absorptive wound dressings.

The pressure wraps 10 disclosed herein are applicable to the medical and first aid fields, such as military first aid, outdoor first aid, and/or emergency response. They also may be applied in hospital emergency departments or wards for hemostasis (bleeding control resulting from penetrating or blunt traumatic injury to a human or animal limb), applying direct pressure to wounds, and/or support for sprains or other orthopedic injuries. Specific applications may include applying presently disclosed pressure wraps to apply direct pressure and/or as a tourniquet to treat extremity bleeding, to treat lacerations to the head, trunk, and/or abdomen, and/or for dialysis shunt securement. In some instances, disclosed pressure wraps 10 may be useful for applications other than applying direct pressure or occluding blood flow. For example, pressure wrap 10 may be secured to a first limb of the subject and to a second limb of the subject, to provide rotational stability, such as when the subject's limb is under traction, or in the event that an injury has occurred that requires stabilization. In other examples, disclosed pressure wraps 10 may have utility as a shoulder sling, a swathe, a knee wrap, an ankle wrap, and/or even nonmedical applications, such as a saline bottle pressure applicator, a belt, a roof rack tie down, and/or connecting one object to another.

Methods of using disclosed pressure wraps 10 also are within the scope of the present disclosure. Generally, pressure wraps 10 are secured on a subject by wrapping pressure wrap 10 around the subject, thereby forming a plurality of loops 30 of elongated elastic strap 12 around the subject and applying direct pressure to the subject. Blood flow to a portion of a limb of the subject may be at least partially occluded by supplying sufficient tension to elongated elastic strap 12 during application of pressure wrap 10. Disclosed pressure wraps 10 may be applied to pediatric subjects, adult subjects, and/or animal subjects, such as to the limbs, head, abdomen, extremities, and/or torso of said subjects. In some cases, methods may include noting the time the pressure wrap was applied on a label (e.g., label 52) attached to the pressure wrap.

To secure disclosed pressure wraps 10 to a subject's limb, the limb may be inserted through a first loop of a plurality of loops (e.g., through adjustable loop 14), the adjustable loop may then be tightened around the subject's limb, and then the remainder of the elongated elastic strap may be wrapped around the subject's limb while tension is applied to the elongated elastic strap, thereby forming the plurality of loops around the subject's limb. When so applying the pressure wrap to the subject, the pressure wrap may be positioned with respect to the subject such that the pressure wrap applies direct pressure to the wound site of the subject. Alternatively, the pressure wrap may be positioned such that it is located proximal to the wound site of the subject. Additionally or alternatively, the pressure wrap may be applied to the subject by positioning at least one loop of the plurality of loops directly over the wound site of the subject and positioning at least another loop of the plurality of loops proximal to the wound site. Wrapping the elongated elastic strap to form a plurality of loops may be performed such that the loops are distributed with respect to the subject to spread the pressure applied by the pressure wrap. In other examples, the disclosed pressure wraps may be applied such that one or more loops of the plurality loops are substantially concentric to one another. When applying the pressure wrap to a subject, generally the entire length of the elongated elastic strap is wrapped around the subject, though in some cases only a portion of the length of the elongated elastic strap is wrapped around the subject. The pressure wrap may be applied to the subject such that hooks of the pressure wrap do not contact the subject.

As used herein, the term "and/or" placed between a first entity and a second entity means one of (1) the first entity, (2) the second entity, and (3) the first entity and the second entity. Multiple entities listed with "and/or" should be construed in the same manner, i.e., "one or more" of the entities so conjoined. Other entities may optionally be present other than the entities specifically identified by the "and/or" clause, whether related or unrelated to those entities specifically identified. Thus, as a non-limiting example, a reference to "A and/or B," when used in conjunction with open-ended language such as "comprising" may refer, in one embodiment, to A only (optionally including entities other than B); in another embodiment, to B only (optionally including entities other than A); in yet another embodiment, to both A and B (optionally including other entities). These entities may refer to elements, actions, structures, steps, operations, values, and the like.

As used herein, the phrase "at least one," in reference to a list of one or more entities should be understood to mean at least one entity selected from any one or more of the entity in the list of entities, but not necessarily including at least one of each and every entity specifically listed within the list of entities and not excluding any combinations of entities in the list of entities. This definition also allows that entities may optionally be present other than the entities specifically identified within the list of entities to which the phrase "at least one" refers, whether related or unrelated to those entities specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including entities other than B); in another embodiment, to at least one, optionally including more than one, B, with no A present (and optionally including entities other than A); in yet another embodiment, to at least one, optionally including more than one, A, and at least one, optionally including more than one, B (and optionally including other entities). In other words, the phrases "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" may mean A alone, B alone, C alone, A and B together, A and C together, B and C together, A, B and C together, and optionally any of the above in combination with at least one other entity.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

As used herein the term "configured" mean that the element, component, or other subject matter is designed and/or intended to perform a given function. Thus, the use of the term "configured" should not be construed to mean that a given element, component, or other subject matter is simply "capable of" performing a given function but that the element, component, and/or other subject matter is specifically selected, created, implemented, utilized, programmed, and/or designed for the purpose of performing the function.

As used herein, the phrase, "for example," the phrase, "as an example," and/or simply the term "example," when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

Examples of inventive subject matter according to the present disclosure are described in the following enumerated paragraphs:

A1. A pressure wrap configured to apply a pressure to a subject, the pressure wrap comprising:

an elongated elastic strap having a length extending longitudinally from a proximal end to a distal end, wherein the elongated elastic strap comprises a first side and a second side opposite the first side, wherein at least a portion of the first side comprises pile compatible with hook-and-loop fasteners, wherein at least a portion of the second side comprises pile compatible with hook-and-loop fasteners, wherein the length of the elongated elastic strap is sufficient to allow the elongated elastic strap to be wrapped around the subject to form a plurality of loops, and wherein the elongated elastic strap is configured to be selectively and reversibly extended as it is wrapped around the subject;

an adjustable loop formed in the elongated elastic strap, wherein a size of the adjustable loop is configured to be selectively increased or decreased via an adjustment component, and wherein the adjustable loop is configured to be applied to the subject as a first loop of the plurality of loops;

a plurality of discrete regions of hooks compatible with the pile of the elongated elastic strap, wherein the plurality of discrete regions of hooks are spaced apart from each other along the length of the elongated elastic strap; and a securement configured to selectively and removably secure the distal end of the elongated elastic strap to an intermediate portion of the elongated elastic strap, thereby securing the pressure wrap with respect to the subject, wherein the intermediate portion is positioned between the proximal end and the distal end, wherein the securement is configured to maintain the pressure wrap in position after it is applied to the subject, wherein the securement comprises a manipulatable fastener, and wherein the manipulatable fastener is hand-operated to secure the distal end of the elongated elastic strap to the intermediate portion of the elongated elastic strap.

A1.1. The pressure wrap of paragraph A1, wherein the securement further comprises an automatic fastener configured to automatically secure the distal end of the elongated elastic strap to the intermediate portion when the automatic fastener contacts the intermediate portion of the elongated elastic strap.

A1.2. The pressure wrap of paragraph A1 or A1.1 wherein the manipulatable fastener is configured to be a redundant fastener.

A2. The pressure wrap of any of paragraphs A1-A1.2, wherein the pressure wrap has a resting configuration and an applied configuration, wherein the elongated elastic strap is under tension when the pressure wrap is in the applied configuration, wherein the length of the elongated elastic strap is a resting length when the pressure wrap is in the resting configuration, and wherein the length of the elongated elastic strap is a stretched length when the pressure wrap is in the applied configuration, wherein the stretched length is greater than the resting length.

A3. The pressure wrap of paragraph A2, wherein the stretched length is at least 40% greater than the resting length, at least 50% greater than the resting length, at least 60% greater than the resting length, at least 70% greater than the resting length, at least 80% greater than the resting length, at least 90% greater than the resting length, and/or at least 100% greater than the resting length.

A4. The pressure wrap of any of paragraphs A2-A3, wherein the pressure wrap is configured to apply the pressure to the subject when the pressure wrap is in the applied configuration.

A5. The pressure wrap of paragraph A4, wherein the pressure is sufficient to stop bleeding at a wound site of the subject.

A6. The pressure wrap of paragraph A4 or A5, wherein the pressure is sufficient to at least partially occlude blood flow distal to the pressure wrap.

A6.1. The pressure wrap of any of paragraphs A1-A6, wherein the pressure wrap is configured such that the pressure may be selectively adjusted by adjusting a tension applied to the elongated elastic strap as the pressure wrap is applied to the subject.

A6.2. The pressure wrap of any of paragraphs A1-A6.1, wherein the pressure wrap is configured such that the pressure may be selectively adjusted via adjustment of disbursement of the plurality of loops, thereby adjusting a width of a compression zone over which the pressure wrap applies the pressure to the subject.

A6.3. The pressure wrap of paragraph A6.2, wherein the pressure wrap is configured such that the width of the compression zone may be expanded with each incremental loop of the plurality of loops as the pressure wrap is applied to the subject.

A6.4. The pressure wrap of any of paragraphs A1-A6.3, wherein the pressure wrap is configured such that the pressure may be selectively decreased by incrementally unwrapping one or more loops of the plurality of loops of the pressure wrap after it has been applied to the subject.

A7. The pressure wrap of any of paragraphs A1-A6.4, wherein an/the automatic fastener of the securement comprises a pull-tab coupled to the elongated elastic strap.

A8. The pressure wrap of any of paragraphs A1-A7, wherein an/the automatic fastener of the securement comprises hooks configured to engage with the pile of the elongated elastic strap within the intermediate portion of the elongated elastic strap.

A9. The pressure wrap of any of paragraphs A1-A8, wherein the manipulatable fastener of the securement comprises a safety pin.

A9.1. The pressure wrap of paragraph A9, wherein the manipulatable fastener is coupled to an/the automatic fastener of the securement.

A9.2. The pressure wrap of paragraph A9 or A9.1, wherein the manipulatable fastener is configured for redundant, or backup, securing of the pressure wrap.

A9.3. The pressure wrap of any of paragraphs A1-A9.2, wherein an/the automatic fastener of the securement comprises adhesive and/or a magnet.

A9.4. The pressure wrap of any of paragraphs A1-A9.3, wherein the manipulatable fastener of the securement comprises a clip, a hook, a snap, a pin, a tie, a clasp, and/or a button.

A10. The pressure wrap of any of paragraphs A1-A9.4, wherein the securement comprises a label configured to receive information about a time at which the pressure wrap is applied to the subject.

A11. The pressure wrap of any of paragraphs A1-A10, wherein the pressure wrap is configured such that the first side of the elongated elastic strap is configured to be positioned facing the subject when the pressure wrap is applied to the subject for at least the first loop.

A11.1. The pressure wrap of any of paragraphs A1-A11, wherein the pressure wrap is configured such that the second side of the elongated elastic strap does not contact the subject when the pressure wrap is applied to the subject.

A12. The pressure wrap of any of paragraphs A1-A11.1, wherein the pressure wrap is configured to apply pressure to the subject regardless of whether the first side or the second side of the elongated elastic strap faces the subject when the pressure wrap is applied to the subject.

A13. The pressure wrap of any of paragraphs A1-A12, wherein the adjustment component is coupled to the second side of the elongated elastic strap.

A14. The pressure wrap of any of paragraphs A1-A13, wherein the second side comprises the plurality of discrete regions of hooks.

A14.1. The pressure wrap of any of paragraphs A1-A14, wherein the plurality of discrete regions of hooks are configured to inhibit or prevent unintentional reduction in the pressure applied by the pressure wrap during application of the pressure wrap to a subject.

A15. The pressure wrap of any of paragraphs A1-A14.1, wherein the plurality of discrete regions of hooks comprises one or more spots of material comprising hooks, wherein each spot of material comprising hooks is coupled to the second side of the elongated elastic strap.

A16. The pressure wrap of any of paragraphs A1-A15, wherein an/the automatic fastener of the securement comprises a first fastener side parallel with the first side of the elongated elastic strap, and wherein the automatic fastener comprises a second fastener side parallel with the second side of the elongated elastic strap.

A17. The pressure wrap of paragraph A16, wherein the first fastener side comprises a/the label configured to receive information about a time at which the pressure wrap is applied to the subject.

A18. The pressure wrap of paragraph A16 or A17, wherein the second fastener side comprises hooks configured to engage the pile of the elongated elastic strap.

A19. The pressure wrap of any of paragraphs A1-A18, wherein the adjustment component comprises a buckle.

A19.1. The pressure wrap of paragraph A19, wherein the buckle is removably coupled to the elongated elastic strap.

A19.2. The pressure wrap of any of paragraphs A19-A19.1, wherein the buckle comprises:

an anchor bar configured to anchor the buckle to the elongated elastic strap;

a slider bar configured to engage the elongated elastic strap and create a direction change therein, such that the adjustable loop is formed when the elongated elastic strap is engaged with the slider bar to create the direction change therein; and a push bar engaged with the proximal end of the elongated elastic strap, wherein the push bar is configured to inhibit pinching of the subject as the pressure wrap is applied to the subject.

A19.3. The pressure wrap of any of paragraphs A19-A19.2, wherein the anchor bar is configured to removably couple the buckle to the elongated elastic strap.

A19.4. The pressure wrap of any of paragraphs A19-A19.3, wherein the buckle comprises a first space between the push bar and the slider bar, wherein the buckle is configured to receive a portion of the elongated elastic strap in the first space.

A20. The pressure wrap of any of paragraphs A19-A19.4, wherein the buckle comprises a second space between the anchor bar and the slider bar, wherein the buckle is configured to receive a portion of the elongated elastic strap in the second space.

A21. The pressure wrap of any of paragraphs A19-A20, wherein the push bar is selectively removable from a pocket formed in the proximal end of the elongated elastic strap.

A22. The pressure wrap of any of paragraphs A19-A21, wherein the push bar is at least substantially covered by the proximal end of the elongated elastic strap.

A23. The pressure wrap of any of paragraphs A19-A22, wherein the anchor bar is substantially parallel to the push bar.

A24. The pressure wrap of any of paragraphs A19-A23, wherein the anchor bar and the push bar are oriented substantially perpendicular to the length of the elongated elastic strap when the buckle is engaged with the elongated elastic strap.

A25. The pressure wrap of any of paragraphs A19-A24, wherein the slider bar is curved.

A26. The pressure wrap of any of paragraphs A19-A25, wherein the buckle comprises an elongated member arranged parallel to the length of the elongated elastic strap when the buckle is engaged with the elongated elastic strap.

A27. The pressure wrap of paragraph A26, wherein the anchor bar, the slider bar, and the push bar extend from the elongated member.

A28. The pressure wrap of paragraph A26 or A27, wherein the anchor bar is positioned at a distal buckle end of the buckle.

A29. The pressure wrap of any of paragraphs A26-A28, wherein the push bar is positioned at a proximal buckle end of the buckle.

A30. The pressure wrap of any of paragraphs A26-A29, wherein the slider bar is positioned in between the anchor bar and the push bar.

A31. The pressure wrap of any of paragraphs A1-A30, wherein the buckle is configured to allow one-handed application of the pressure wrap to the subject.

A32. The pressure wrap of any of paragraphs A19-A31, wherein the elongated elastic strap comprises an anchor slot to receive the anchor bar.

A33. The pressure wrap of paragraph A32, wherein the anchor slot comprises hooks configured to engage the pile of the elongated elastic strap.

A34. The pressure wrap of any of paragraphs A32-A33, wherein the anchor slot extends at least substantially transverse to the length of the elongated elastic strap.

A35. The pressure wrap of any of paragraphs A32-A34, wherein the anchor bar comprises a J-bend configured to prevent unintentional removal of the anchor bar from the anchor slot.

A36. The pressure wrap of any of paragraphs A1-A35, wherein the elongated elastic strap comprises pile along at least substantially the entire length of the elongated elastic strap.

A37. The pressure wrap of any of paragraphs A1-A36, wherein the elongated elastic strap has a strap width perpendicular to the length of the elongated elastic strap.

A38. The pressure wrap of paragraph A37, wherein the elongated elastic strap comprises pile covering at least a majority of the strap width on the first side of the elongated elastic strap.

A39. The pressure wrap of paragraph A37 or A38, wherein the elongated elastic strap comprises pile covering at least a majority of the strap width on the second side of the elongated elastic strap.

A40. The pressure wrap of any of paragraphs A1-A39, wherein the pile of the elongated elastic strap comprises one or more strips of pile compatible with hook-and-loop fasteners.

A41. The pressure wrap of paragraph A40, wherein the pressure wrap comprises one or more strips of pile compatible with hook-and-loop fasteners on the first side of the elongated elastic strap.

A42. The pressure wrap of paragraph A40 or A41, wherein the pressure wrap comprises one or more strips of pile compatible with hook-and-loop fasteners on the second side of the elongated elastic strap.

A43. The pressure wrap of any of paragraphs A40-A42, wherein the one or more strips of pile extend substantially parallel to the length of the elongated elastic strap.

A44. The pressure wrap of any of paragraphs A1-A43, wherein a/the slider bar of the adjustment component is configured to retain the elongated elastic strap about the slider bar and assist in forming the adjustable loop.

A45. The pressure wrap of any of paragraphs A1-A44, wherein a/the slider bar of the adjustment component comprises an upper catch that extends from the slider bar towards a/the anchor bar of the adjustment component, wherein the upper catch is configured to retain the elongated elastic strap in a/the second space between the slider bar and the anchor bar.

A46. The pressure wrap of any of paragraphs A1-A45, wherein a/the slider bar of the adjustment component comprises a lower catch that extends from the slider bar towards a/the push bar of the adjustment component, wherein the lower catch is configured to retain the elongated elastic strap in a/the first space between the slider bar and the push bar.

A47. The pressure wrap of any of paragraphs A1-A46, wherein the adjustment component comprises a/the buckle, and wherein a buckle width of the buckle is at most a/the strap width of the elongated elastic strap.

A48. The pressure wrap of any of paragraphs A1-A47, wherein a/the strap width of the elongated elastic strap is at most 1 inch, at most 1.1 inches, at most 1.2 inches, at most 1.3 inches, at most 1.4 inches, at most 1.5 inches, at most 1.6 inches, at most 1.7 inches, at most 1.8 inches, at most 1.9 inches, at most 2 inches, at most 2.5 inches, at most 3 inches, at most 4 inches, and/or at most 5 inches.

A49. The pressure wrap of any of paragraphs A1-A48, wherein the length of the elongated elastic strap in a/the resting configuration is at least 1 foot, at least 1.5 feet, at least 2 feet, at least 2.5 feet, at least 3 feet, at least 3.5 feet, at least 4 feet, at least 4.5 feet, at least 5 feet, at least 5.5 feet, at least 6 feet, at least 6.5 feet, at least 7 feet, at least 7.5 feet, and/or at least 8 feet.

A50. The pressure wrap of any of paragraphs A1-A49, wherein the length of the elongated elastic strap in an/the applied configuration is at least 2 feet, at least 3 feet, at least 4 feet, at least 5 feet, at least 6 feet, at least 7 feet, at least 8 feet, at least 9 feet, at least 10 feet, at least 11 feet, at least 12 feet, at least 13 feet, at least 14 feet, at least 15 feet, and/or at least 16 feet.

A51. The pressure wrap of any of paragraphs A1-A50, wherein the length of the elongated elastic strap is sufficient such that the elongated elastic strap may be wrapped around the subject to form at least 2 loops, at least 3 loops, at least 4 loops, at least 5 loops, at least 6 loops, at least 7 loops, at least 8 loops, at least 9 loops, and/or at least 10 loops.

A52. The pressure wrap of any of paragraphs A1-A51, further comprising a carrying pouch configured to store the pressure wrap when not in use.

A53. The pressure wrap of any of paragraphs A1-A52, wherein the pressure wrap is configured to apply pressure to pediatric, adult, and animal subjects.

A54. The pressure wrap of any of paragraphs A1-A53, wherein the pressure wrap is one size fits all.

A55. The pressure wrap of any of paragraphs A1-A54, wherein the pressure wrap is configured to apply direct pressure to a/the wound site of the subject.

A56. The pressure wrap of any of paragraphs A1-A55, wherein the pressure wrap is configured to serve as a tourniquet.

A57. The pressure wrap of any of paragraphs A1-A56, wherein the pressure wrap is configured for multiple uses.

A58. The pressure wrap of any of paragraphs A1-A57, wherein the pressure wrap may be used as a shoulder sling, a swathe, a knee wrap, an ankle wrap, a saline bottle pressure applicator, a belt, and/or a roof rack tie down.

A59. The pressure wrap of any of paragraphs A1-A58, wherein the pressure wrap is configured for single use.

A60. The pressure wrap of any of paragraphs A1-A59, wherein the elongated elastic strap is configured for single use and the adjustment component is configured for multiple uses.

A61. The pressure wrap of any of paragraphs A1-A60, wherein the adjustment component is configured to be sterilized in an autoclave.

A62. The pressure wrap of any of paragraphs A1-A61, wherein the adjustment component comprises stainless steel.

A63. The pressure wrap of any of paragraphs A1-A62, wherein the adjustment component comprises a/the buckle, and wherein the buckle has a contoured shape configured to conform to the subject.

A64. The pressure wrap of any of paragraphs A1-A63, wherein the adjustment component is configured to resiliently deform during application of the pressure wrap.

A65. The pressure wrap of any of paragraphs A1-A64, wherein the elongated elastic strap comprises a visualization window configured to allow viewing of a/the wound site of the subject as the pressure wrap is applied to the subject.

A66. The pressure wrap of any of paragraphs A1-A65, wherein the pressure wrap is configured to be applied to the subject such that each loop of the plurality of loops of the elongated elastic strap is substantially concentric with the other loops of the plurality of loops.

A67. The pressure wrap of any of paragraphs A1-A66, wherein the pressure wrap is configured to be applied to the subject such that each loop of the plurality of loops may be positioned to spread and/or distribute a/the pressure applied by the pressure wrap.

A68. The pressure wrap of any of paragraphs A1-A67, wherein the pressure wrap may be applied to the subject without the adjustment component.

A69. The pressure wrap of any of paragraphs A1-A68, wherein the pressure wrap is configured for self-application by the subject.

A70. The pressure wrap of any of paragraphs A1-A69, wherein the pressure wrap is configured to be gradually removed from the subject.

A71. The pressure wrap of any of paragraphs A1-A70, wherein a/the pressure applied by the pressure wrap is selectively continuously adjustable by selectively adjusting an amount of tension applied to the elongated elastic strap during application.

A72. The pressure wrap of any of paragraphs A1-A71, wherein the adjustment component comprises a sleeve coupled to the elongated elastic strap, wherein the sleeve defines a passage through which the elongated elastic strap is free to longitudinally translate prior to forming the plurality of loops, wherein the proximal end of the elongated elastic strap is coupled to an interior surface of the sleeve, and wherein the adjustable loop is formed by positioning a length of the elongated elastic strap proximal to the sleeve, with the distal end of the elongated elastic strap being positioned distal to the sleeve.

A73. The pressure wrap of paragraph A72, wherein the sleeve is a tubular sleeve.

A74. The pressure wrap of any of paragraphs A1-A73, wherein a longitudinal axis of the sleeve is at least substantially parallel to the length of the elongated elastic strap.

A75. The pressure wrap of any of paragraphs A1-A74, wherein a diameter of the passage of the sleeve is transverse to the length of the elongated elastic strap.

A76. The pressure wrap of any of paragraphs A1-A75, wherein the sleeve comprises one or more discrete regions of hooks compatible with the pile of the elongated elastic strap.

A77. The pressure wrap of any of paragraphs A1-A76, wherein the sleeve comprises gauze.

A78. The pressure wrap of any of paragraphs A1-A77, wherein the sleeve comprises a flexible fabric material, an elastic material, and/or a webbing.

A79. The pressure wrap of any of paragraphs A1-A78, wherein the size of the adjustable loop is configured to be selectively increased by translating the elongated elastic strap with respect to the sleeve such that the distal end of the elongated elastic strap moves closer to the sleeve.

A80. The pressure wrap of any of paragraphs A1-A79, wherein the size of the adjustable loop is configured to be selectively decreased by translating the elongated elastic strap with respect to the sleeve such that the distal end of the elongated elastic strap is moved further away from the sleeve.

B1. A method, comprising:
providing the pressure wrap of any of paragraphs A1-A80; and
securing the pressure wrap on the subject by wrapping the pressure wrap around the subject, thereby forming the plurality of loops of the elongated elastic strap around the subject and applying direct pressure to the subject.

B2. The method of paragraph B1, further comprising at least partially occluding blood flow to a portion of a limb of the subject by supplying sufficient tension to the elongated elastic strap during application of the pressure wrap.

B3. The method of any of paragraphs B1-B2, wherein the subject is a pediatric subject, an adult subject, or an animal subject.

B4. The method of any of paragraphs B1-B3, wherein the securing the pressure wrap comprises securing the pressure wrap around a/the limb of the subject.

B5. The method of any of paragraphs B1-B4, wherein the securing the pressure wrap comprises applying the pressure wrap to the subject's head, abdomen, extremities, or torso.

B6. The method of any of paragraphs B1-B5, further comprising labeling a time of application of the pressure wrap on a/the label of the pressure wrap.

B7. The method of any of paragraphs B1-B6, wherein the securing the pressure wrap comprises inserting a/the limb of the subject through a/the first loop of the plurality of loops, wherein the first loop is formed by engagement of the elongated elastic strap with the adjustment component.

B8. The method of any of paragraphs B1-B7, wherein the securing the pressure wrap comprises positioning the pressure wrap with respect to the subject such that the pressure wrap applies direct pressure to a/the wound site of the subject.

B9. The method of any of paragraphs B1-B8, wherein the securing the pressure wrap comprises positioning the pressure wrap such that it is located proximal to a/the wound site of the subject.

B10. The method of any of paragraphs B1-B9, wherein the securing the pressure wrap comprises positioning at least one loop of the plurality of loops directly over a/the wound site of the subject and positioning at least another loop of the plurality of loops proximal to the wound site.

B11. The method of any of paragraphs B1-B10, wherein the securing the pressure wrap comprises wrapping the elongated elastic strap to form a plurality of substantially concentric loops around the subject.

B12. The method of any of paragraphs B1-B11, wherein the securing the pressure wrap comprises wrapping the elongated elastic strap to form a plurality of loops that are distributed with respect to the subject to spread a/the pressure applied by the pressure wrap.

B13. The method of any of paragraphs B1-B12, wherein the securing the pressure wrap comprises wrapping the entire length of the elongated elastic strap around the subject.

B14. The method of any of paragraphs B1-B13, wherein the securing the pressure wrap comprises wrapping the pressure wrap such that the first side of the elongated elastic strap is positioned against the subject.

B15. The method of any of paragraphs B1-B14, wherein the securing the pressure wrap comprises wrapping the pressure wrap such that hooks of the pressure wrap do not contact the subject.

B16. The method of any of paragraphs B1-B15, wherein the securing the pressure wrap comprises securing the pressure wrap to a first limb of the subject and to a second limb of the subject to provide rotational stability.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, when the disclosure or subsequently filed claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are believed to be novel and non-obvious. Inventions embodied in other combinations and subcombinations of features, functions, elements and/or properties may be claimed through amendment of those claims or presentation of new claims in that or a related application. Such amended or new claims, whether they are directed to a different invention or directed to the same invention, whether different, broader, narrower or equal in scope to the original claims, are also regarded as included within the subject matter of the inventions of the present disclosure.

The invention claimed is:
1. A pressure wrap configured to apply a pressure to a subject, the pressure wrap comprising:
an elongated elastic strap having a length extending longitudinally from a proximal end to a distal end, wherein the elongated elastic strap comprises a first side and a second side opposite the first side, wherein at least a portion of the first side comprises pile compatible with hook-and-loop fasteners, wherein at least a portion of the second side comprises pile compatible with hook-and-loop fasteners, wherein the length of the elongated elastic strap is sufficient to allow the elongated elastic strap to be wrapped around the subject to form a plurality of loops, and wherein the elongated elastic strap is configured to be selectively and reversibly extended as it is wrapped around the subject;
an adjustable loop formed in the elongated elastic strap, wherein a size of the adjustable loop is configured to be selectively increased or decreased via an adjustment component, and wherein the adjustable loop is configured to be applied to the subject as the first loop of the plurality of loops;
a plurality of discrete regions of hooks compatible with the pile of the elongated elastic strap, wherein the plurality of discrete regions of hooks are spaced apart from each other along the length of the elongated elastic strap; and
a securement configured to selectively and removably secure the distal end of the elongated elastic strap to an intermediate portion of the elongated elastic strap, thereby securing the pressure wrap with respect to the subject, wherein the securement is configured to maintain the pressure wrap in position after it is applied to the subject, and wherein the securement comprises a manipulatable fastener, wherein the manipulatable fastener is hand-operated to secure the distal end of the elongated elastic strap.

2. The pressure wrap according to claim 1, wherein the pressure wrap has a resting configuration and an applied configuration, wherein the elongated elastic strap is under tension when the pressure wrap is in the applied configuration, wherein the length of the elongated elastic strap is a resting length when the pressure wrap is in the resting configuration, and wherein the length of the elongated elastic strap is a stretched length when the pressure wrap is in the applied configuration, and wherein the stretched length is at least 40% greater than the resting length.

3. The pressure wrap according to claim 2, wherein the pressure wrap is configured to apply the pressure to the subject when the pressure wrap is in the applied configuration, and wherein the pressure is sufficient to stop bleeding at a wound site of the subject by applying direct pressure to the wound site.

4. The pressure wrap according to claim 3, wherein the pressure is sufficient to at least partially occlude blood flow distal to the pressure wrap.

5. The pressure wrap according to claim 1, wherein the pressure wrap is configured such that the pressure may be selectively adjusted by adjusting a tension applied to the elongated elastic strap as the pressure wrap is applied to the subject.

6. The pressure wrap according to claim 1, wherein the pressure wrap is configured such that the pressure may be selectively adjusted via adjustment of disbursement of the plurality of loops, thereby adjusting a width of a compression zone over which the pressure wrap applies the pressure to the subject.

7. The pressure wrap according to claim 6, wherein the pressure wrap is configured such that the width of the compression zone may be expanded with each incremental loop of the plurality of loops as the pressure wrap is applied to the subject.

8. The pressure wrap according to claim 1, wherein the pressure wrap is configured such that the pressure may be selectively decreased by incrementally unwrapping one or more loops of the plurality of loops of the pressure wrap after it has been applied to the subject.

9. The pressure wrap according to claim 1, wherein the manipulatable fastener is a redundant fastener, and wherein the securement further comprises an automatic fastener configured to automatically secure the distal end of the elongated elastic strap when the automatic fastener contacts the intermediate portion of the elongated elastic strap.

10. The pressure wrap according to claim 9, wherein the automatic fastener comprises a pull-tab coupled to the elongated elastic strap, wherein the pull-tab comprises hooks configured to engage with the pile of the elongated elastic strap.

11. The pressure wrap according to claim 9, wherein the automatic fastener comprises a label configured to receive information about a time at which the pressure wrap is applied to the subject.

12. The pressure wrap according to claim 1, wherein the pressure wrap is configured such that the first side of the elongated elastic strap is configured to be positioned facing the subject when the adjustable loop is applied to the subject, and wherein the securement is coupled to the second side of the elongated elastic strap.

13. The pressure wrap according to claim 1, wherein the second side comprises the plurality of discrete regions of hooks configured to engage the pile of the elongated elastic strap, and wherein the plurality of discrete regions of hooks are configured to inhibit unintentional reduction in the pressure applied by the pressure wrap during application of the pressure wrap to the subject.

14. The pressure wrap according to claim 1, wherein the adjustment component comprises a buckle, and wherein the buckle comprises:
   an anchor bar configured to anchor the buckle to the elongated elastic strap;
   a slider bar configured to engage the elongated elastic strap and create a direction change therein, such that the adjustable loop is formed when the elongated elastic strap is engaged with the slider bar to create the direction change therein; and
   a push bar engaged with the proximal end of the elongated elastic strap, wherein the push bar is configured to inhibit pinching of the subject as the pressure wrap is applied to the subject.

15. The pressure wrap according to claim 14, wherein the buckle comprises a first space between the push bar and the slider bar, wherein the buckle is configured to receive a portion of the elongated elastic strap in the first space, wherein the buckle comprises a second space between the anchor bar and the slider bar, and wherein the buckle is configured to receive a portion of the elongated elastic strap in the second space.

16. The pressure wrap according to claim 14, wherein the push bar is selectively removable from a pocket formed in the proximal end of the elongated elastic strap, and wherein the push bar is at least substantially covered by the proximal end of the elongated elastic strap.

17. The pressure wrap according to claim 14, wherein the anchor bar is substantially parallel to the push bar, wherein the anchor bar and the push bar are oriented substantially perpendicular to the length of the elongated elastic strap when the buckle is engaged with the elongated elastic strap.

18. The pressure wrap according to claim 14, wherein the buckle comprises an elongated member arranged parallel to the length of the elongated elastic strap when the buckle is engaged with the elongated elastic strap, wherein the anchor bar, the slider bar, and the push bar extend from the elongated member, wherein the anchor bar is positioned at a distal buckle end of the buckle, wherein the push bar is positioned at a proximal buckle end of the buckle, and wherein the slider bar is positioned in between the anchor bar and the push bar.

19. The pressure wrap according to claim 14, wherein the elongated elastic strap comprises an anchor slot to receive the anchor bar, wherein the anchor slot comprises hooks configured to engage the pile of the elongated elastic strap.

20. The pressure wrap according to claim 1, wherein the adjustment component is configured to allow one-handed application of the pressure wrap to the subject.

21. The pressure wrap according to claim 1, wherein the elongated elastic strap comprises pile along at least substantially the entire length of the elongated elastic strap.

22. The pressure wrap according to claim 1, wherein the adjustment component comprises a sleeve coupled to the elongated elastic strap, wherein the sleeve defines a passage through which the elongated elastic strap is free to longitudinally translate prior to forming the plurality of loops, wherein the proximal end of the elongated elastic strap is coupled to an interior surface of the sleeve, and wherein the adjustable loop is formed by positioning a length of the elongated elastic strap proximal to the sleeve, with the distal end of the elongated elastic strap being positioned distal to the sleeve.

23. The pressure wrap according to claim 22, wherein a longitudinal axis of the sleeve is at least substantially parallel to the length of the elongated elastic strap, and wherein a diameter of the passage of the sleeve is transverse to the length of the elongated elastic strap.

24. The pressure wrap according to claim 22, wherein the sleeve comprises one or more discrete regions of hooks compatible with the pile of the elongated elastic strap.

25. The pressure wrap according to claim 22, wherein the size of the adjustable loop is configured to be selectively increased by translating the elongated elastic strap with respect to the sleeve such that the distal end of the elongated elastic strap moves closer to the sleeve, and wherein the size of the adjustable loop is configured to be selectively decreased by translating the elongated elastic strap with respect to the sleeve such that the distal end of the elongated elastic strap is moved further away from the sleeve.

26. The pressure wrap according to claim 1, wherein the pressure applied by the pressure wrap is selectively continuously adjustable by selectively adjusting an amount of tension applied to the elongated elastic strap during application, and wherein the pressure wrap is configured such that pressure may be reduced by incrementally unwrapping the pressure wrap from the subject.

* * * * *